(12) United States Patent
Friberg et al.

(10) Patent No.: US 8,921,367 B2
(45) Date of Patent: Dec. 30, 2014

(54) USE OF AMG 900 FOR THE TREATMENT OF CANCER

(71) Applicant: Amgen Inc., Thousand Oaks, CA (US)

(72) Inventors: Gregory Friberg, Westlake Village, CA (US); Marc Payton, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/906,231

(22) Filed: May 30, 2013

(65) Prior Publication Data

US 2013/0323198 A1    Dec. 5, 2013

Related U.S. Application Data

(60) Provisional application No. 61/654,021, filed on May 31, 2012.

(51) Int. Cl.
| | | |
|---|---|---|
| *A61K 31/506* | (2006.01) | |
| *A61K 38/19* | (2006.01) | |
| *A61K 45/06* | (2006.01) | |

(52) U.S. Cl.
CPC .............. *A61K 31/506* (2013.01); *A61K 45/06* (2013.01); *A61K 38/193* (2013.01)
USPC ......................................... 514/248; 514/13.5

(58) Field of Classification Search
CPC .................................................. A61K 31/506
See application file for complete search history.

(56) References Cited

U.S. PATENT DOCUMENTS

| | | |
|---|---|---|
| 7,560,551 B2 | 7/2009 | Cee et al. |
| 2007/0185111 A1* | 8/2007 | Cee et al. ....................... 514/241 |

FOREIGN PATENT DOCUMENTS

WO    WO2011/031842 A1    3/2011

OTHER PUBLICATIONS

Carducci et al. Journal of Clinical Oncology, (May 20, 2012) vol. 30, No. 15, Supp. Suppl. 1. (Abstract attached).*
Bush et al. Proceedings of the American Association for Cancer Research Annual Meeting, (Apr. 2010) vol. 51, pp. 1076. Meeting Info.: 101st Annual Meeting of the American-Association-for-Cancer-Research. Washington, DC, USA. Apr. 17-21, 2010. Amer Assoc Canc Res. (Abstract attached).*
Paller et al., "Preclinical Profile of AMG900 in Combination with HDACIs in Prostate Cancer", AACR, 2012, poster.
Search results of , 2013 "Use of AMG 900 for the Treatment of Cancer" based on U.S. Appl. No. 13/906,231.
Payton et al., "Antitumor Activity of AMG 900, an Orally Available Small Molecule Inhibitor of Aurora Kinases, Alone and in Combination with Tubulin-targeting Agents in Human Metastatic Breast Cancer", Abstract #3556, AACR, Orlando, FL; Apr. 2-6, 2011.
Bush et al. (2010), "Preclinical Characterization of AMG 900, an Orally Bioavailable Small Molecule Inhibitor of Aurora Kinases in Phase 1 Clinical Trails", AACR, poster.
Ziegler et al., "Preclinical Pharmacokinetic and Biomarker Analysis of AMG 900, an Orally Bioavailable Small Molecule Inhibitor of Aurora Kinases, in Human Xenograft Tumor and Surrogate Tissues", Abstract#3600, AACR, Washington DC; Apr. 17-21, 2010.
Geuns-Meyer et al., Discovery of AMG 900: a highly selective, orally bioavailable inhibitor of aurora kinases with efficacy in preclinical antitumor models and activity against multidrug resistant cells, AACR 101st Annual Meeting, Apr. 21, 2010.
Friedberg et al. (2014), "Phase II study of Alisertib, a Selective Aurora A Kinase Inhibitor, in Relapsed and Refractory Aggressive B- and T-cell Non-Hodgkin Lymphomas", Journal of Clinical Oncology, 32(1):44-51.
Cheung et al., "AMG 900, a Potent and Highly Selective Aurora Kinase Inhibitor Shows Promising Preclinical Activity Against Acute Myeloid Leukemia Cell Lines in Vitro and in Vivo", ASH, 2013.
Payton et al., "Preclinical Evaluation of AMG 900, a Novel Potent and Highly Selective Pan-Aurora Kinase Inhibitor with Activity in Taxane-Resistant Tumor Cell Lines", Cancer Res; 70(23) Dec. 1, 2010. doi:10.1158/0008-5472.CAN-10-3001.
Huang et al., "In vitro and in vivo pharmacokinetic characterizations of AMG 900, an orally bioavailable small molecule inhibitor of aurora kinases", Xenobiotica, 2011; 41(5): 400-408. Doi: 10.3109/00498254.2010.548534.
Bush et al., "In Vivo Characterization of AMG 900, an Orally Active Small Molecule Inhibitor of Aurora Kinases in Phase 1 Clinical Trials" Departments of Oncology Research and Medicinal Chemistry, Amgen Inc., USA, 2009.
Schellens, et al., "Phase 1 and pharmacological study of the novel aurora kinase inhibitor AZD1152", ASCO Annual Meeting 2006.
Schellens, et al., "A Phase 1 Study of the novel Aurora Kinase inhibitor AZD1152 in advanced solid malignancies", ASCO 2006.
Renshaw et al., "A phase 1 two arm trial of AS703569 (R763), an orally available aurora kinase inhibitor, in subjects with solid tumors: preliminary results", ASCO Annual Meeting 2007.
Hidalgo et al., "A Phase I Study of MK-0646, a Humanized Monoclonal Antibody Against the Insulin-like Growth Factor Receptor Type 1 (IGF-1R) in Advanced Solid Tumor Patients in a q2 wk Schedule", ASCO 2008.

(Continued)

*Primary Examiner* — James D Anderson
(74) *Attorney, Agent, or Firm* — G. Prabhakar Reddy

(57) ABSTRACT

The present invention relates to methods of using AMG 900, a small molecule pan aurora kinase inhibitor, for the treatment of cancer, including solid tumors, hematologically derived tumors and the like. The invention further provides pharmaceutical compositions, dosage ranges and treatment regimens for administering AMG 900 to treat cancer.

31 Claims, 5 Drawing Sheets

(56) References Cited

OTHER PUBLICATIONS

Atzoni et al., "A phase 1 pharmacokinetic and pharmacodynamics study of weekly MK-0646, an Insulin Like Growth Factor-1 Receptor (IGF-1R) monoclonal antibody in patients with advanced solid tumors (Study P001)", ASCO 2008.

Jones et al., "Phase I accelerated dose-escalation, pharmacokinetic (PK) and pharmacodynamics study of PF-03814735, an oral aurora kinase inhibitor, in patients with advanced solid tumors: Preliminary results ASCO 2008 Phase I PF-03814735 Abstract", ASCO 2008.

Carducci et al., "First-in-human Study of AMG 900, an Oral Pan-Aurora Kinase Inhibitor, in Adult Patients With Advanced Solid Tumors", ASCO, Chicago, IL; Jun. 1-5, 2012.

Cohen et al., "A Phase 1 Dose-Escalation Study of Danusertib (PHA-739358) Administered as a 24-Hour Infusion with and without Granulocyte Colony-Stimulation Factor in a 14-Day Cycle in Patients with Advanced Solid Tumors", Clin Cancer Res 2009;15(21) Nov. 2009.

Hilton et al., "Aurora Kinase Inhibition As an Anticancer Strategy", Journal of Clinical Oncology, vol. 32, No. 1 (Jan. 1, 2014), : pp. 57-59.

* cited by examiner

Figure 1-a
Absolute Measure
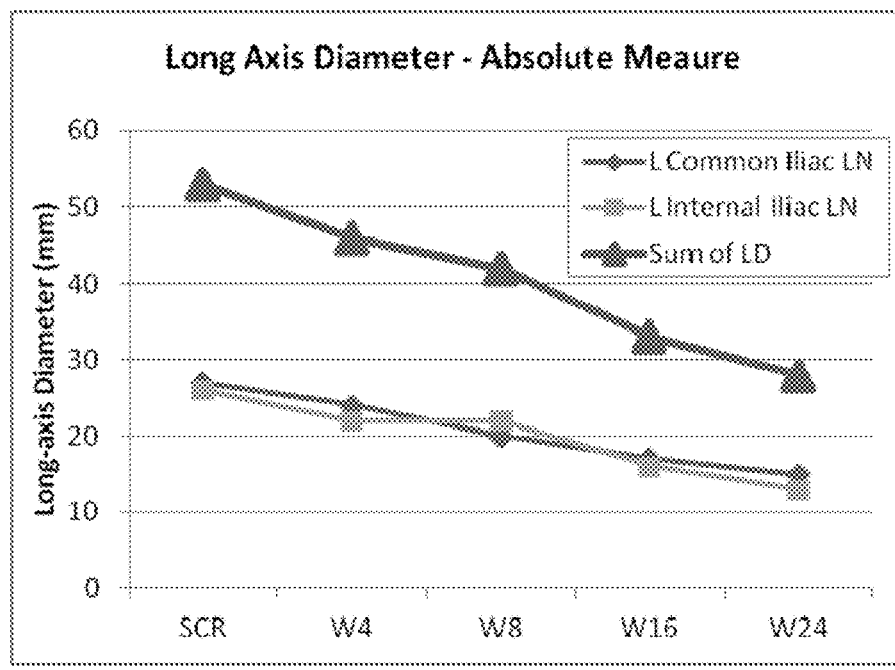
Figure 1-b
% Change
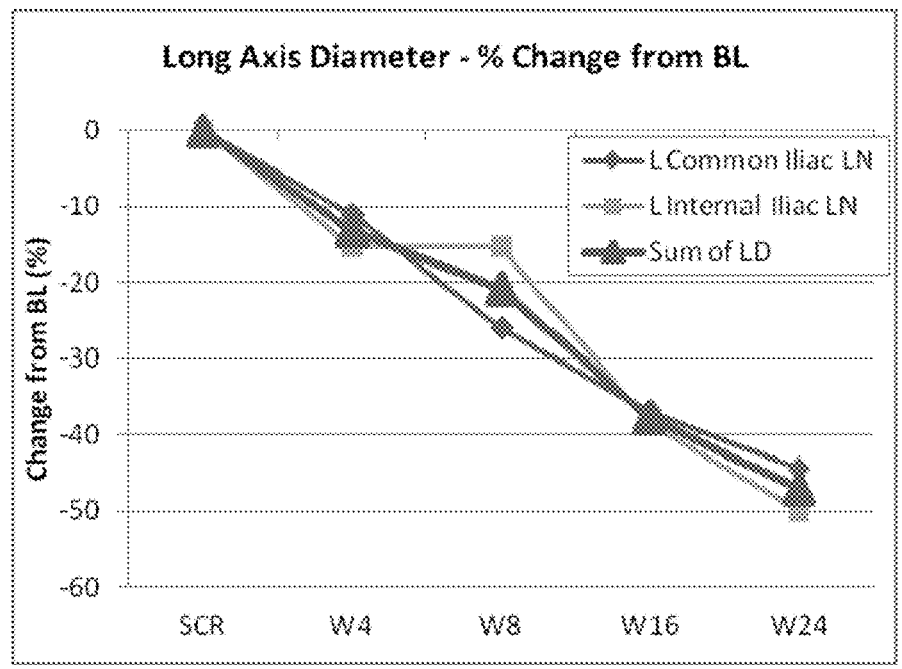

Figure 2-a
Absolute Measure
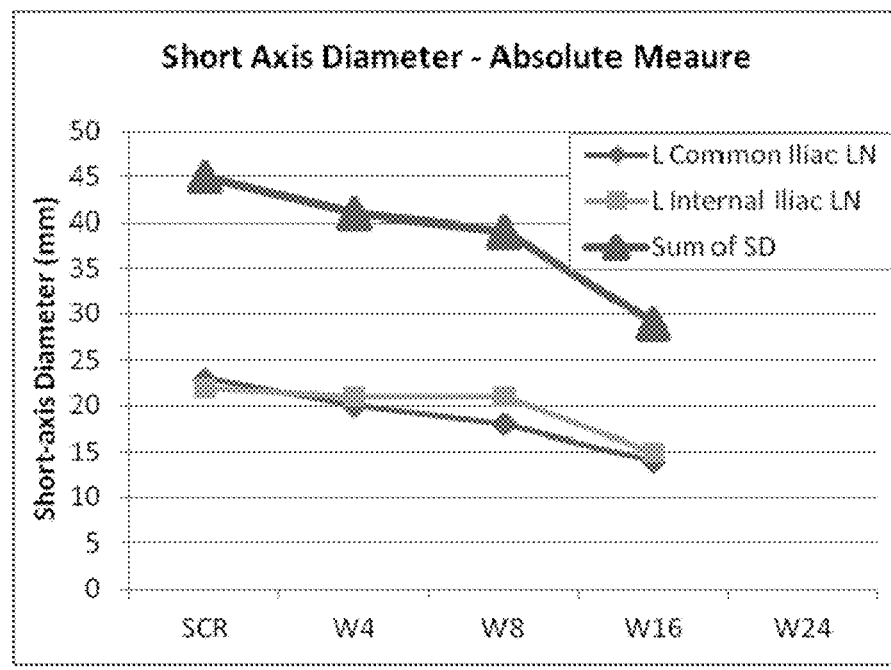
Figure 2-b
% Change
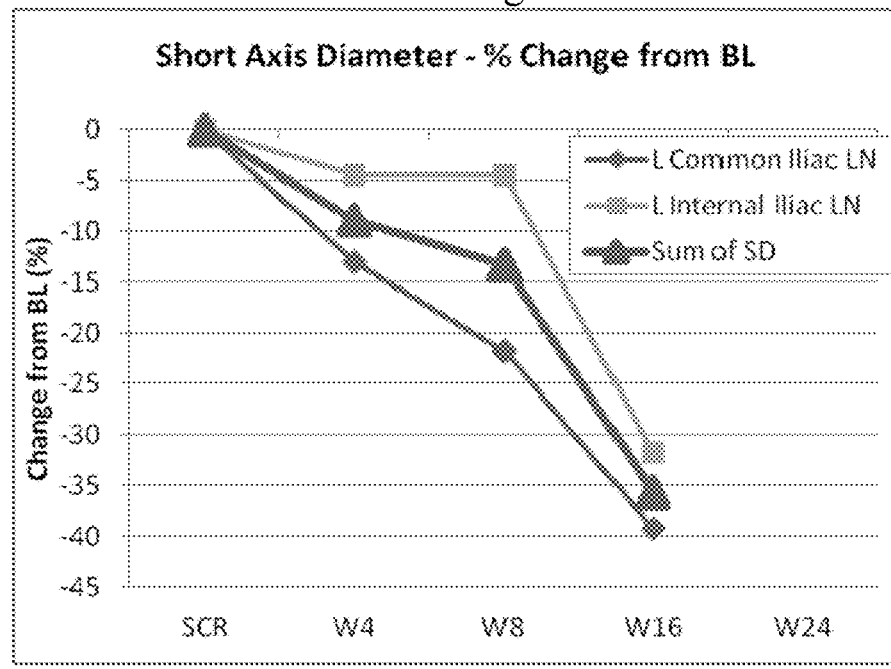

Figure 3-a
Absolute Measure
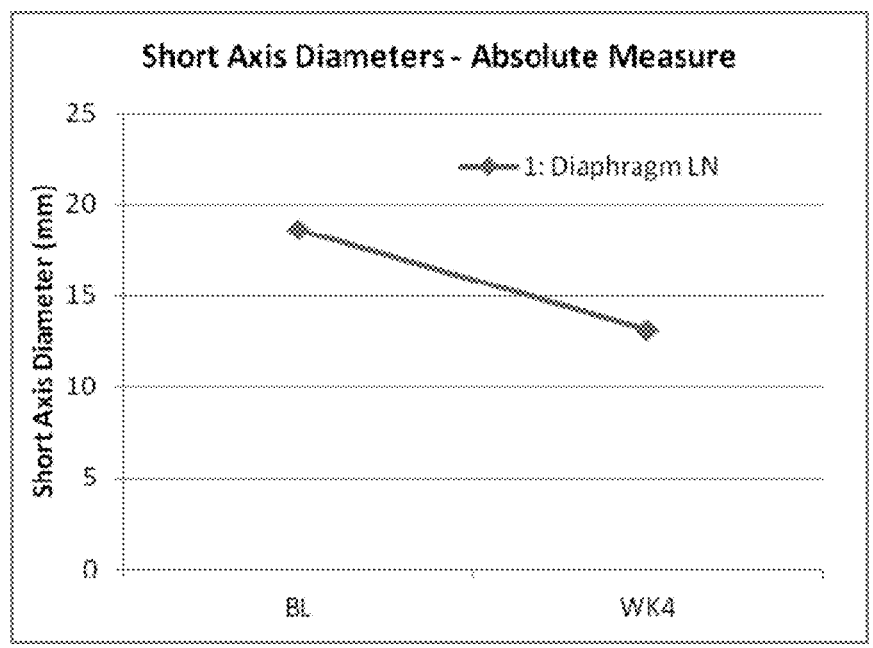
Figure 3-b
% Change
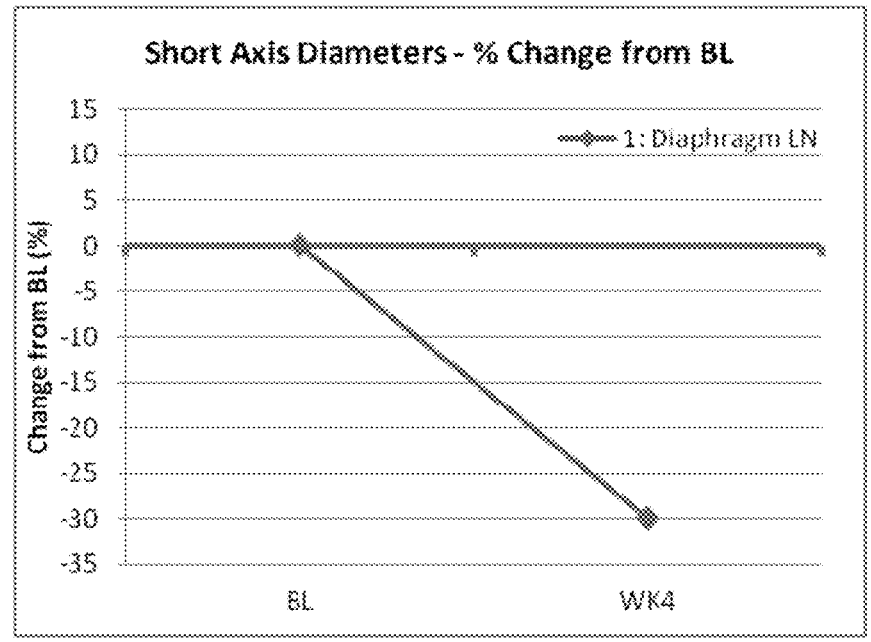

Figure 4-a
Absolute Measure
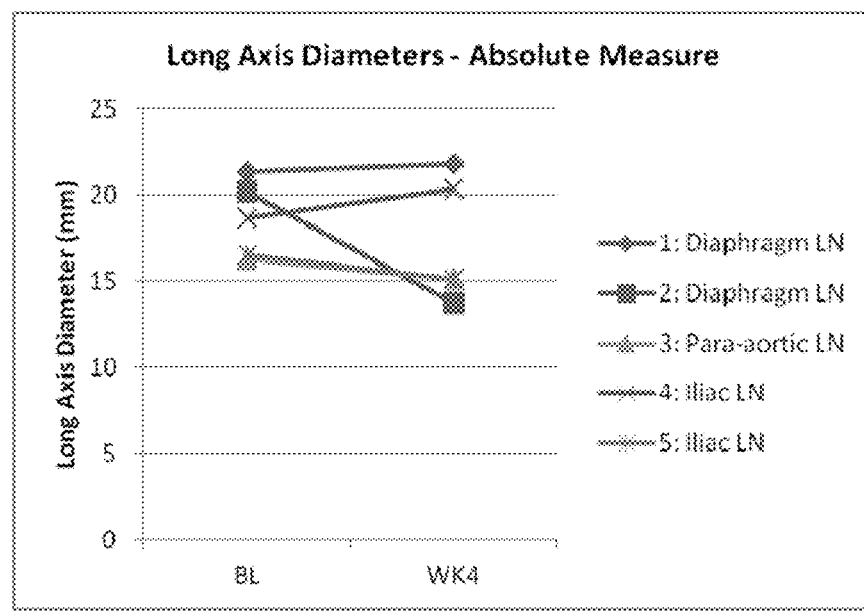
Figure 4-b
% Change
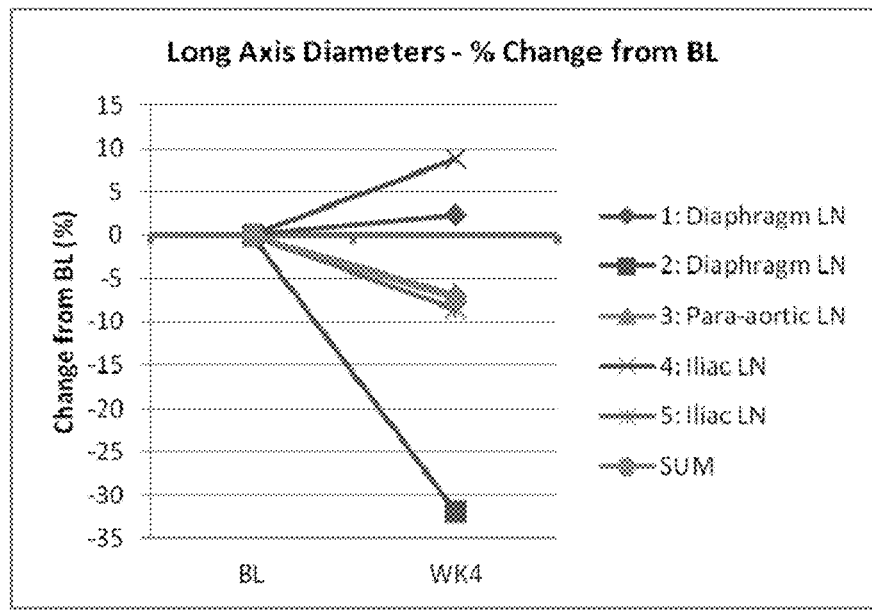

Figure 5-a
Absolute Measure
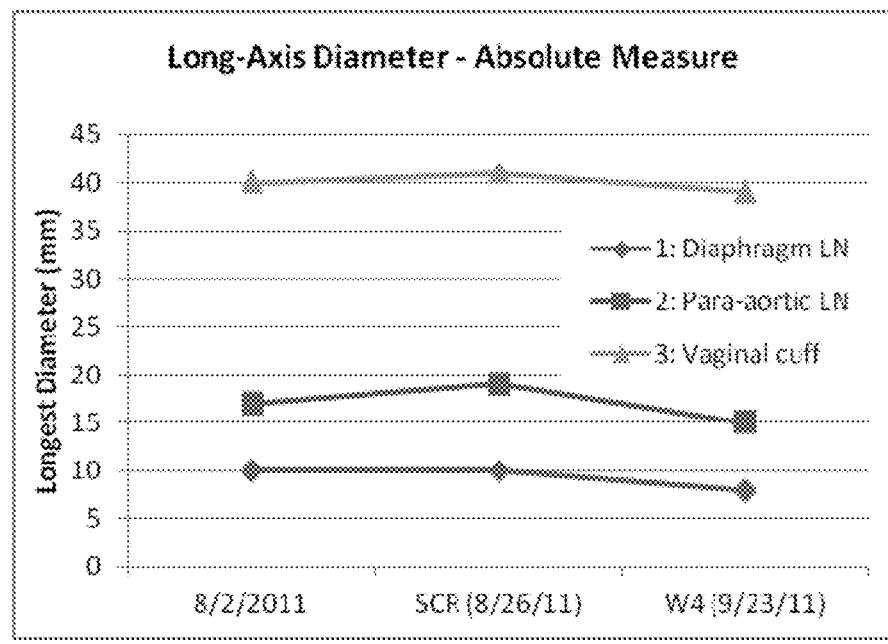
Figure 5-b
% Change
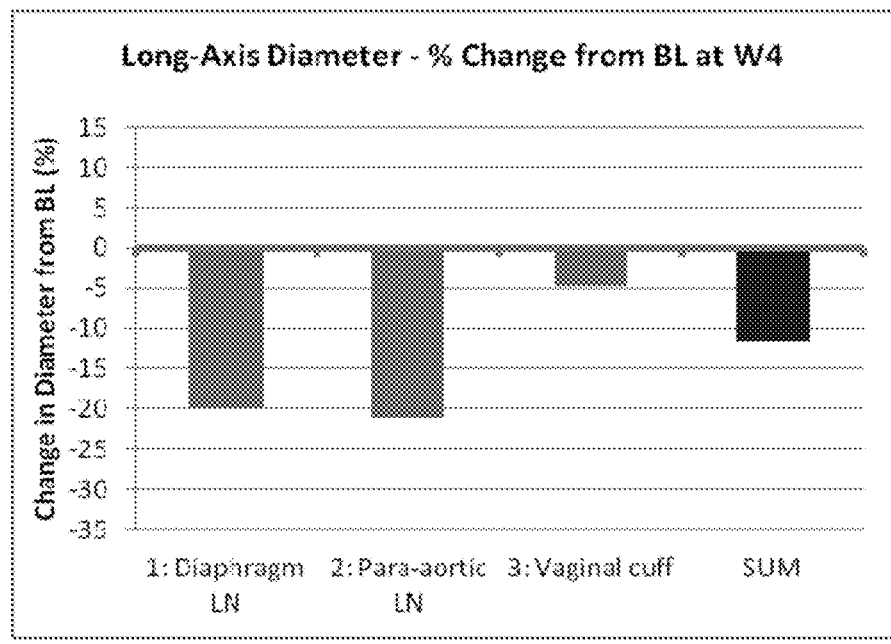

USE OF AMG 900 FOR THE TREATMENT OF CANCER

FIELD OF THE INVENTION

The present invention relates to the use of AMG 900, N-(4-((3-(2-amino-4-pyrimidinyl)-2-pyridinyl)oxy)phenyl)-4-(4-methyl-2-thienyl)-1-phthalazinamine, for the treatment of cancer.

BACKGROUND OF THE INVENTION

Cancer is one of the most widespread diseases affecting mankind, and a leading cause of death worldwide. In the United States alone, cancer is the second leading cause of death, surpassed only by heart disease. Cancer is often characterized by deregulation of normal cellular processes or unregulated cell proliferation. Cells that have been transformed to cancerous cells tend to proliferate in an uncontrolled and unregulated manner leading to, in some cases, metastisis or the spread of the cancer. Deregulation of the cell proliferation could result from the modification to one or more genes, responsible for the cellular pathways that control cell-cycle progression. Or it could result from DNA modifications (including but not limited to mutations, amplifications, rearrangements, deletions, and epigenetic gene silencing) in one or more cell-cycle checkpoint regulators which allow the cell to move from one phase of the cell cycle to another unchecked.

Somatic cell division is a complex and highly coordinated process that ensures faithful segregation of duplicated chromosomes into two daughter cells. Deregulation of the cell cycle is a hallmark of cancer, characterized by uncontrolled proliferation and defects in chromosome segregation. Mitosis is the process by which a eukaryotic cell segregates its duplicated chromosomes into two identical daughter nuclei. It is generally followed immediately by cytokinesis, which divides the nuclei, cytoplasm, organelles and cell membranes into two daughter cells containing roughly equal shares of these cellular components. Mitosis and cytokinesis together define the mitotic (M) phase of the cell cycle—the division of the mother cell into two daughter cells, genetically identical to each other and to their parent cell.

The process of mitosis is complex and highly regulated. The sequence of events is divided into distinct phases, corresponding to the completion of one set of activities and the start of the next. These stages are prophase, prometaphase, metaphase, anaphase and telophase. During the process of mitosis duplicated chromosomes condense and attach to fibers that pull the sister chromatids to opposite sides of the cell. The cell then divides in cytokinesis, to produce two identical daughter cells. Errors in mitosis can either kill a cell through apoptosis or cause mis-segratation of chromosomes that may lead to cancer.

Normally, cell-cycle checkpoints are activated if DNA errors are detected (e.g. DNA damage). If these errors to the genome cannot be fixed, the cell normally undergoes apoptosis. However, if the cell is allowed to move through its cell-cycle and progress unchecked, then more mutations can accumulate over time. These gene modifications can accrue and eventually leading cell progeny with pre-malignant or malignant neoplastic characteristics (e.g. uncontrolled proliferation) through adaptation.

Antimitotic drugs that block tumor cell division are a proven intervention strategy in the treatment of cancer. However, the clinical benefits of classical antimitotic drugs may be hampered by development of multidrug resistance (MDR) and collateral damage to non-dividing cells including for example, peripheral neuropathy (Quasthoff S. et al, Chemotherapy-Induced Peripheral Neuropathy, *J. Neurol.* 249: 9-17, 2002).

Aurora kinases are essential mitotic regulators and their potential role in tumorigenesis makes them attractive targets for anticancer therapy (Keen N. et al, Aurora-kinase Inhibitors as Anti-cancer Agents, *Nat. Rev. Cancer*, 4:927-936, 2004; Keen N. et al, Mitotic Drivers—Inhibitors of the Aurora B Kinase, *Cancer Met. Rev.*, 28:185-195, 2009; and Carvahjal R D. et al, Aurora-Kinases: New Targets for Cancer Therapy, *Clin. Cancer Res.* 12:6869-6875, 2006). In mammalian cells, the aurora family of serine/threonine protein kinases is comprised of three paralogous genes (aurora-A, -B, and -C). Aurora-A and -B are essential regulators of mitotic entry and progression, whereas aurora-C function is primarily restricted to male meiosis during spermatogenesis. Aurora-A can function as an oncogene and is amplified in a subset of human tumors. Aurora-A and -B expression is frequently elevated in human cancers and is associated with advanced clinical staging (Gautschi et al, *Clin. Cancer Res.*, 14:1639-1648, 2008). The mitotic checkpoint, also referred to as the spindle assembly checkpoint (SAC), is a surveillance mechanism responsible for controlling proper alignment, microtubule-kinetochore attachments, and segregation of duplicated chromosomes. In tumor cells, genetic depletion or pharmacological inhibition of aurora-A results in abnormal spindle formation and SAC activation. In constrast, depletion or inhibition of aurora-B inactivates the SAC, resulting in aborted cell division without a mitotic arrest. Importantly, dual suppression of aurora-A and -B appears to phenocopy the effects of inhibiting aurora-B alone (Hauf S. et al., *J. Cell Biol.* 161:281-194, 2003; and Yang H. et al, *FEBS Letters*, 579: 3385-3391, 2005). The silencing of the SAC leads to an accumulation of tumor cells that contain 4N DNA content in the G1-phase of the cell cycle. Continued suppression of aurora-B activity leads to further rounds of genome replication without division, a process referred to as endoreduplication, which ultimately results in tumor cell death (Girdler F. et al, *J. Cell Sci.*, 119:3664-3675, 2006).

The therapeutic window is very important for the success of a drug in treating a patient. Generally, the pharmacokinetic (PK) and pharmacodynamic (PD) factors of a given drug will help determine what the therapeutic window for that drug may be, in a subject or in an animal or human. Pharmacokinetic factors include, for example, plasma (blood) drug concentration per unit time; tissue drug concentration (per unit time); drug metabolism including, without limitation, the absorption, distribution (in both tissues and serum); protein binding, clearance, elimination, drug interactions and the like, of the drug; route of clearance; and drug half life, to name a few. Pharmacodynamic factors involve factors relating to the desired therapeutic effect of the drug and/or the duration of action of the drug on the target. For instance, some pharmacodynamic factors include, without limitation, binding affinity or potency of the drug for the receptor(s) or target(s); reaction dynamics between the drug and the biological target; mode of action of the drug on the target.

Other factors influencing the therapeutic window of a drug include and, therefore the successful treatment of the patient with the drug, for instance, body size, age, gender, route of administration, time of administration, tolerance, barometric pressure, gastrointestinal function, fever, liver function, diet; stress, breastfeeding, other drugs, disease, cardiovascular function, starvation, exercise, age, sunlight, pregnancy, immunologic function, kidney function, genetic make-up, immunization, alcohol intake, albumin level in the blood, smoking, and weight. These are but a few considerations that doctors must consider when prescribing a drug with the objective of providing the maximum benefit to the patient.

Each of these factors play a role, complexly interwoven, in attempting to determine whether or not a drug has a therapeutic window in subjects, such as in humans, and if one does exists, how wide or how large that therapeutic dosage range or window of therapeutic beneficial effect it may be. It is known that generally in order for a drug to possess a sufficient therapeutic margin, it must have sufficient target coverage. That is, it must be acting on the biological target at a sufficient concentration and over a sufficient time period, per day, to drive the beneficial/therapeutic effect on the disease or condition, while not inducing or causing an unacceptable level of undesired and/or untreatable side effects. Despite some understanding in general of how many of these factors influence one another in-vivo, every drug, i.e., every molecule per se is a different structure and has its own distinct pK and PD profiles and, to this end, will have a unique and unpredictable in-vivo safety and efficacy profile.

Historically, the task of finding a suitable therapeutic window for a specific molecule, and one that provides sufficient confidence in success to justify the investment and time, has been difficult and very unpredictable in nature. First, therapeutic windows in which to administer a drug is unique to that particular molecule. Second, this window must be shown to be statistically significant and meaningful in human clinical trials, which take years to enroll and complete and required a great amount of time, resources and investment without any certainty of success.

There have been a few aurora kinase targeted therapeutics clinically tested. Each was found to possess a different potential therapeutic window, if one was identified at all. For instance, Danusertib (PHA-739358), a pan-aurora kinase inhibitor, was dosed in a Ph I trial to assess its safety, tolerability, pharamcokinetics and pharmacodynamic profile. Dosing schedule began with a 24 hour infusion every 14 days. It was concluded from the trial that danusertib can be safely administered to patients with advanced refractory solid tumors upto an amount of 500 mg/m$^2$ over 24 hours in a 14 day cycles without GCSF. Within this dose, danusertib was found to provide "prolonged objective response in small cell lung carcinoma and multiple instance of prolonged disease stabilization in other solid tumors (Cohen et al, *Clinical Cancer Res.,* 15(21), 2009). Thus, a therapeutic window was identified for this potential drug.

Another example is the study of PF-03814735, an oral auaroa kinse inhibitor in a Ph I study for pK and PD in patients with advanced solid tumor. In that trial PF-03814735 was administered in a daily dosing schedule of 5 or 10 consecutive days in 3-week cycles. This means that the inhibitor was dosed for either 5 consecutive days followed by 16 days without any dosing, or for 10 consecutive days followed by 11 days without any drug. Patients had various solid tumors, including colorectal, breast, non-small cell lung cancer, small cell lung cancer, bladder, melanoma, ovarian, renal, and head and neck tumors. A safety margin for PF-03814735 was identified, as adverse events began to be observed during the dose escalation phase. However, the dosing schedule tested provided NO objective response on the tumors. Thus, no therapeutic window for that particular dosing schedule was identified for this specific molecule (Jones et al., *J. Clin. Onc.* Vol. 26, 2008). The dosages administered were raised in certain circumstances in a hope to identify a therapeutic window.

Yet another example of how unpredictable it is to identify a suitable therapeutic window for a given molecule is that of Renshaw and co-workers. Renshaw and colleagues disclosed some results from the Ph I trial of AS703569 (R763), an orally available aurora kinase inhibitor in subjects with solid tumors. The compounds was administered according to two dosing regimens over a 3-week or 12 day cycle: (1) dosing on days 1 and 8, i.e., dose for one day on day 1 followed by off for days 2-7, then dose again on day 8, followed by no dosing on days 9-21 to complete the cycle; and (2) consecutive dosing on days 1, 2 and 3, followed by no dosing on days 4-21 of the 3-week cycle. Patient solid tumors included uterine/cervical cancer and 2 cases of breast cancer. The drug was found to be tolerable at various dosages in the regimen schedules tested (Renshaw et al., *J. Clin. Onc.*, vol 25, No. 18S, 2007). However, no positive impact(s) on the patient's solid tumors were reported. Hence, it is reasonable to conclude that no therapeutic window was identified for this compound due to a lack of any sign of drug efficacy on patient tumors.

Another example of that of MK-5108. MK-5108 is an aurora kinase inhibitor, selective for aurora A kinase. It was clinically tested in humans in a Ph I trial wherein the dosing schedule was as follows: the drug was orally administered every 12 hrs during the first 1 days of each cycle, and the cycle length was 14-21 days. Hence, patients received drug every 12 hours for 2 consecutive days and did not receive drug for the remaining 12 (or 19) days in the cycle (US Clinicaltrials.gov). It was ultimately determined that the product was maximally beneficial if administered in combination with docetaxol (IV; *Mol. Cancer. Ther.,* 1 (9), 157-166, 2010). Hence, as a potential first line, stand alone therapeutic, no suitable therapeutic window was reported, and it is believed that one was not identified, for this molecule.

Another example is AZD1152, a specific-aurora kinase inhibitor, selective for auroroa B, was dosed in a Ph I trial to assess its safety, tolerability, pharamcokinetics and pharmacodynamic profile. Dosing schedule began with a 2 hour IV infusion every 7 days (weekly). It was concluded from the trial that AZD 1152 was safely administered to patients with advanced solid malignancies upto a dosage amount of 450 mg. Within this dose, AZD1152 was observed to "significantly stabilize disease" in patients with rapidly progressive diseases (Schellens et al, *J. Clinical One.,* 24(18S), 2006). Thus, it was concluded that there was sufficient information to continue to develop the molecule, in the hope that a suitable therapeutic window would be identified.

Patient compliance with taking a particular drug is an important factor in the successful treatment of that patient's medical condition, state and/or disease. It doesn't necessarily matter, generally, whether or not that treatment is merely prophylactic or whether that treatment is either acute or chronic. Patients tend to follow treatment schedules or treatment regimens that are convenient, easy to administer and/or easily remembered. For example, oral dosage forms intended to be administered or taken by the patient once a day, with or without a meal, is generally regarded as a convenient regimen with a high likelihood of patient compliance. However, such a once-a-day regiment may not be optimal dosing period to address the patients' conditions, symptoms and/or disease, such as cancer. Thus, there is a need to identify the optimal dosage amount of a drug to be administered in a convenient dosing schedule or regimen, to provide best patient compliance with treatment for cancer.

AMG 900 is an orally bioavailable, potent and selective pan-aurora kinase inhibitor which has anti-cancer properties in tumor cells. Particularly, AMG 900 has exhibited uniform potency across various tumor cell lines, including P-gp and BCRP expressing cell lines. In vivo, AMG 900 blocks the phosphorylation of histone H3, a proximal substrate of aurora-B (Crosio C. et al, *Mol. Cell. Bio.* 22:874-885, 2002)

and inhibits the growth of multiple tumor xenografts, including three MDR xenograft models resistant to paclitaxel or docetaxel. AMG 900 is presently under clinical evaluation in adult patients with cancer, including advanced solid tumors, and in adult patients with myelogenous leukemias, both acute (AML) and chronic (CML).

It is unknown what any specific anti-cancer therapeutic agent may afford with respect to being able to treat, or even improve upon and/or provide superior treatments for, cancer over the standard of care cancer treatment at the time of filing this application. To this end, there is always a need to develop the best, most effective dosing regimen for a given drug, to most effectively treat cancer while minimizing undesired side effects and patient non-compliance with the medication. In addition, there is a need to improve upon the current available treatments or provide better, more efficiaous treatment schedules, and/or more convenient or easier to comply with treatment regimens, for cancer patients.

BRIEF DESCRIPTION OF THE DRAWINGS/FIGURES

FIGS. 1-*a* and 1-*b* depicts the positive effects of orally administered AMG 900 on a patient with stage IV solid endometrial cancerous tumor as measured by its long axis diameter;

FIGS. 2-*a* and 2-*b* depicts the positive effects of orally administered AMG 900 on a patient with stage IV solid endometrial cancerous tumor as measured by its short axis diameter;

FIGS. 3-*a* and 3-*b* depicts the positive effects of orally administered AMG 900 on a patient with stage IV-B solid ovarian cancerous tumor as measured by its short axis diameter;

FIGS. 4-*a* and 4-*b* depicts the positive effects of orally administered AMG 900 on a patient with stage IV-B solid ovarian cancerous tumor as measured by its long axis diameter per a central read;

FIGS. 5-*a* and 5-*b* depicts the positive effects of orally administered AMG 900 on a patient with a stage IV-B solid ovarian cancerous tumor as measured by its long axis diameter per a local read.

BRIEF DESCRIPTION OF THE INVENTION

The present invention provides for use of AMG 900 (also referred to herein as "the compound"), or a pharmaceutically acceptable salt form thereof, for the treatment of cancer. Particularly, when AMG 900 was administered to a subject or cancer patient in a specific dosage regimen comprising a dose of AMG 900 within a certain range, the patient exhibited an unexpected and surprising positive response or effect on their cancer from treatment with AMG 900. More specifically, it was unexpectedly discovered that AMG 900 when administered to cancer patients in certain dosage ranges over a certain treatment regimen slowed the growth and/or progression of various solid tumor cancers in patients. Such a positive tumor response may translate into optimal dosages administered to the cancer patient in convenient to administer and/or more compliant dosage regimens. In this manner, dosing AMG 900 by the present invention for the treatment of cancer not only affords a surprisingly effective dosing regimen for treating the cancer, but may also represents an improvement in compliance by, and of convenience for, the patient. Such improvements can translate into a cost savings for the patient in that such treatment places the patient in a superior or even the best position for long-term survival with improved quality of life.

AMG 900 has a chemical name of N-(4-((3-(2-amino-4-pyrimidinyl)-2-pyridinyl)oxy)phenyl)-4-(4-methyl-2-thienyl)-1-phthalazinamine and is represented by the structure:

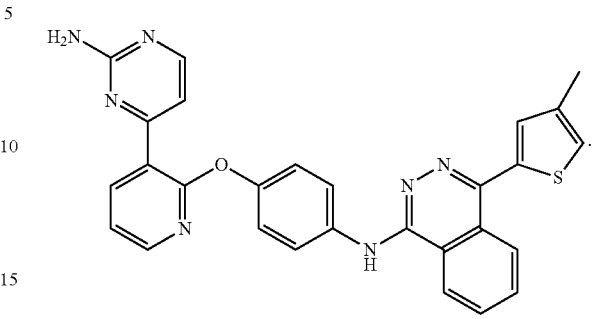

The invention further provides use of a pharmaceutical composition comprising this compound, or a pharmaceutically acceptable salt form thereof, for therapeutic, prophylactic, acute or chronic treatment of cancer, including solid tumors of prostate cancer, breast cancer, ovarian cancer, uterine cancer, endometrial cancer, lung cancer and the like, and other proliferating cancerous cells in patients. In one embodiment, the invention provides the use of AMG 900 in the manufacture of medicaments, and of pharmaceutical compositions, for the treatment of cancer in subjects who are in need of treatment. The invention further contemplates using AMG 900 in combination with such HDAC inhibitors presently approved for medical use by regulatory agencies, including without limitation Vorinostat and Romidepsin, as well as other HDAC agents undergoing clinical trials, including without limitation Panobinostat (LBH589), Valproic acid (as Mg valproate); Belinostat (PXD101), Mocetinostat (MGCD103), Abexinostat (PCI-24781), Entinostat (MS-275), SB939, Resminostat (4SC-210), Givinostat (ITF2357), CUDC-101, AR-42, CHR-2845, CHR-3996, 4SC-202, CG200745, ACY-1215 and Sulforaphane. The invention also includes use of any other pre-clinical HDAC inhibitors determined useful for the treatment of cancer via the reduction or inhibition of histone deacetylase activity in combination with AMG 900 for the treatment of cancer.

In another embodiment, the invention provides a method of treating a solid tumor, including non-small cell lung cancer, breast cancer, and prostate cancer in a subject, the method comprising administering AMG 900, or a pharmaceutically acceptable salt thereof, in a dosage regimen to the subject, the dosage regimen comprising administering to the subject a dose of AMG 900 ranging from about 1 mg to about 50 mg. In other embodiments, the dosage amount of AMG 900 administered to the subject ranges from about 1.5 mg to about 45 mg. In yet another embodiment, the dose of AMG 900 administered to the subject ranges from about 5 mg to about 45 mg. In yet another embodiment, the dose of AMG 900 administered to the subject ranges from about 10 mg to about 40 mg. In yet another embodiment, the dose of AMG 900 administered to the subject ranges from about 15 mg to about 40 mg. In yet another embodiment, the dose of AMG 900 administered to the subject ranges from about 16 mg to about 35 mg. In yet another embodiment, the dose of AMG 900 administered to the subject ranges ranges from about 16 mg to about 24 mg. In yet another embodiment, the dose of AMG 900 administered to the subject ranges ranges from about 16 mg to about 30 mg. In yet another embodiment, the dose of AMG 900 administered to the subject is about 16 mg. In yet another embodiment, the dose of AMG 900 administered to the subject about 24 mg. In yet another embodiment, the dose of AMG 900 administered to the subject ranges ranges from about 5 mg to about 100 mg.

In another embodiment, the invention provides the method described hereinabove wherein the dosage regimen comprises orally administering the dose of AMG 900 to the subject once daily for 3, 4, 5, 6, 7, 8, 9 or 10 consecutive days or the patient is "on" AMG 900 once daily for 3, 4, 5, 6, 7, 8, 9 or 10 consecutive days. In other embodiments, the regimen further comprises non-treatment of AMG 900 for a period ranging from 6 days to 20 days immediately following the once daily consecutive day treatment of AMG 900, or the patient is "off" of AMG 900 dosing for a period ranging from 6 days to 20 days immediately following the once daily consecutive day treatment. In yet further embodiments, the invention provides methods wherein the dosage regimen comprises orally administering the dose of AMG 900 to the subject once daily for 4, 5, 6 or 7 consecutive days followed immediately by non-treatment of AMG 900 for a period ranging from 6 days to 20 days, or even orally administering the dose of AMG 900 to the subject once daily for 4 or 7 consecutive days followed immediately by non-treatment of AMG 900 for a period ranging from 6 days or 15 days. The invention further provides additional embodiments of varying dosing regimen or dosing schedules are described hereinbelow.

DETAILED DESCRIPTION OF THE INVENTION

AMG 900, a small molecule pan Aurora A, B and C kinase inhibitor, has been found to provide a surprising and unexpected positive response in subjects suffering from various types of cancer, including various advanced solid tumors, when dosed in a certain dosage regimen comprising a dose of AMG 900 within a specific dosage range. More specifically, it was unexpectedly discovered that AMG 900 when administered to cancer patients in doses ranging from about 1 mg to about 50 mg for a certain consecutive daily on-off dosing period (specified treatment regimen) slowed the growth and/or progression of the tumor in the patient. Accordingly, the present invention provides for uses of AMG 900 in treating cancer by administering AMG 900 in a dose within a certain range in compliance with a specified dosing regimen.

DEFINITIONS

The following definitions should further assist in understanding the scope of the invention described herein.

The terms "cancer" and "cancerous" when used herein refer to or describe the physiological condition in subjects that is typically characterized by unregulated cell growth. Examples of cancer include, without limitation, carcinoma, lymphoma, sarcoma, blastoma and leukemia. More particular examples of such cancers include squamous cell carcinoma, lung cancer, pancreatic cancer, cervical cancer, ovarian cancer, uterine cancer, bladder cancer, hepatoma, breast cancer, colon carcinoma, and head and neck cancer. While the term "cancer" as used herein is not limited to any one specific form of the disease, it is believed that the combination treatment methods provided by the invention will be particularly effective for a variety of cancers in a subject in need of treatment.

The term "HDAC inhibiting agent" when used herein refers to a histone deacetylase inhibiting agent, which alone, may be useful for treating cancer. This term additionally refers to antineoplastic drugs used to treat cancer or a combination of these drugs into a standardized treatment regimen. Examples of HDAC inhibiting agents include, without limitation, member agents of Classes I-IV. For instance, examples of HDAC inhibiting agents include, without limitation, those which are approved for human use such as Vorinostat and Romidepsin, those which have been regulatorily approved for and are undergoing human clinical trials such as Panobinostat (LBH589; Ph III for various cancers including cutaneous T-cell lymphoma), valproic acid (administered as Mg valproate salt; in Ph III trials for cervical and ovarian cancer); Belinostat (PXD101; Ph II trial for relapsed ovarian cancer, and reportedly good results for T cell lymphoma), Mocetinostat (MGCD103; undergoing Ph II clinical trials for various cancers, including follicular lymphoma, Hodgkin lymphoma and acute myeloid leukemia (AML)), Abexinostat (PCI-24781; undergoing Ph II clinical trial for sarcoma and lymphoma), Entinostat (MS-275; undergoing clinical trials Hodgkin lymphoma, lung cancer and breast cancer), SB939 (In Ph II for recurrent or metastic prostate cancer (HRPC), and ahs shown good Ph II results for myelofibrosis), Resminostat (4SC-201; exhibited good results for Hodgkin lymphoma, and has met a primary endpoint in a Ph II trial for hepatocellular carcinoma), Givinostat (ITF2357; undergoing clinical trials for refractory leukemias and lyelomas), CUDC-101 (in Ph I for safety and intended for Ph II cancer trials), AR-42 (started clinical traisl for various cancers including relapsed or treatment resistant multpiple myeloma, chronic lymphmocytic leukemia or lymphoma), CHR-2845, CHR-3996, 4SC-202 (for selective hematological indications), CG200745 (in clinical trails for solid tumors), ACY-1215 (in clinical trials for multiple myeloma), and Sulforaphane, a novel histone deacetylase inhibitor in clinical trials as an anti-cancer agent. The invention also includes use of any other pre-clinical HDAC inhibitors, including without limitation, Kevetrin, an agent selective for HDAC2, that are later determined to be useful for the treatment of cancer via the reduction or inhibition of histone deacetylase activity in combination with AMG 900.

The term "comprising" is meant to be open ended, including the indicated component(s) but not excluding other elements.

The term "subject" as used herein refers to any mammal, including humans and animals, such as cows, horses, dogs and cats. Thus, the invention may be used in human patients as well as in veterinarian subjects and patients. In one embodiment of the invention, the subject is a human.

The phrase "effective dosage amount" or "therapeutically-effective" when used in conjunction with AMG 900, or a second anti-cancer agent, is intended to quantify the amount of the compound (AMG 900 or second anti-cancer agent), which will achieve a reduction in the progress of growth of the tumor or cancer, or an actual decrease in size or severity of the cancer or tumor.

The terms "treat", "treating" and "treatment" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The term "positive response" as used herein is intended to refer to a reduction or decrease in physical size of the solid tumor when compared to the physical size of the same tumor at day 1 un-treated or prior to any treatment with AMG 900 (BL or base line). A positive response may also be referred to herein as a partial response.

The term "stable disease" as used herein is intended to refer to a tumor treated with AMG 900 not increasing in size at a rate equivalent to a corresponding un-treated tumor of the same type. This term also means that the size of a given solid tumor has not increased at all or only minimally increased in size between day 1 (BL) and a later treatment day in the dosage schedule/regimen.

The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of the compound may be prepared from an inorganic acid or from an organic acid. Examples of such inorganic acids include, without limitation, hydrochloric, hydrobromic, hydroiodic, nitric, carbonic, sulfuric and phosphoric acid. Examples of organic acids include, without limitation, aliphatic, cycloaliphatic, aromatic, arylaliphatic, heterocyclic, carboxylic and sulfonic classes of organic acids, examples of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxyethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. It is also within the scope of the invention herein to have multiple counter ion salts associate with the free base of AMG 900 and/or the HDAC inhibiting agent. For instance, and without limiting the scope of the invention, a bis-HCl, bis-sulfonic acid, bis-methanesulfonic acid, bis-benzenesulfonic acid, bis-toluenesulfonic acid, bis-aspartic acid, bis-malic acid or a bis-glutamic acid salt of AMG 900 is contemplated herein to be useful alone, or in combination with an HDAC inhibiting agent, to treat cancer.

Suitable pharmaceutically-acceptable base addition salts of the compound include, without limitation, metallic salts such as salts made from aluminum, calcium, lithium, magnesium, potassium, sodium and zinc, or salts made from organic bases including primary, secondary, tertiary amines and substituted amines including cyclic amines such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of the salts contemplated herein may be prepared by conventional means from the corresponding compound by reacting, for example, the appropriate acid or base with the compound. A base addition salt of a carboxylic acid or similar functional group on the HDAC inhibiting agent administered may be useful in carrying out the invention described herein. Some useful HDAC inhibiting agents which may readily form base addition salts include, without limitation, hydroxamic acids or hydroxamates such as trichostatin A, vorinostat (also referred to herein as SAHA), belinostat and panobinostat, and aliphatic acid compounds such as phenyl butyrate and valproic acid.

The term "therapeutic window" (or pharmaceutical window) of a given drug or drug product is the range of dosages which can treat disease effectively while staying within the safety range. In other words, it is the dosages of the drug between the amount that gives an effect (effective dose) and the amount that gives more adverse or undesirable side effects than desired effects. Generally, clinical trial data provides the optimal therapeutic window for a given drug. A "theapeutic window" is, in vivo, a well-defined range of a drug's serum concentration at which a desired beneficial therapeutic effect occurs, below which there is little therapeutic benefit or effect, and above which toxicity occurs. The therapeutic window differs among patients and may be determined empirically. For instance, medication with a small pharmaceutical window such as Tegretol must be administered with care and control, e.g. by frequently measuring blood concentration of the drug, since it easily gives adverse effects such as agranulocytosis. More specifically, it is the range between the $ED_{50}$ and the starting point of $TD_{50}$ curve. It is believed that this index can help to avoid most of the potential side effects. It is worth noting that the window can vary by situation. In some cases, the therapeutic window can even be completely "closed", meaning that the adverse effects exceed the desired effects at all doses capable of providing the desired effect. This is the (politicized) assertion made by governments that prohibit certain drugs: that at any dose, they do more harm than good. This index is believed to be more reliable than either the therapeutic index or the protective index, since this index considers the biological variation among individuals to a larger extent. The downside, however, is that it (like the protective index) also introduces an element of subjectivity.

The term "CT" as used herein is intended to refer to computed tomography images with improved performance, i.e., with improved special resolution (volumetric CT). Volume CT uses a two-dimensional x-ray detector orientation to take multiple two-dimensional images of the tumor being scanned. CT scans are common techniques known in the art.

The term "MI" as used herein is intended to refer to magnetic resonance imaging. Magnetic resonance imaging is a medical technique used in radiology to visualize internal structures of the body in detail. MRI generally provides good contrast between the different soft tissues of the body, which makes it especially useful in imaging the brain, muscles, the heart and cancers in the body. MRI imaging techniques are common techniques known in the art.

AMG 900, N-(4-((3-(2-amino-4-pyrimidinyl)-2-pyridinyl)oxy)phenyl)-4-(4-methyl-2-thienyl)-1-phthalazinamine, may be prepared by the procedure analogous to that described in PCT publication WO2007087276, Example Methods A1 or A2 on pg 70 but using 1-chloro-4-(4-methyl-2-thienyl) phthalazine as the starting material, in conjunction with Examples 15 (pg 50), 25 (pg 55) and 30 (pg 59). These procedures are also described in U.S. Pat. No. 7,560,551, which specification is hereby incorporated herein by reference in its entirety. Specifically, AMG 900 may be prepared as described in Example 1 below.

Example 1

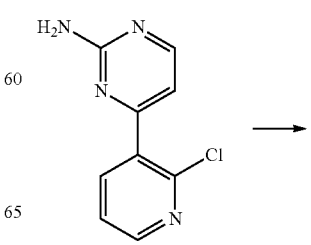

-continued

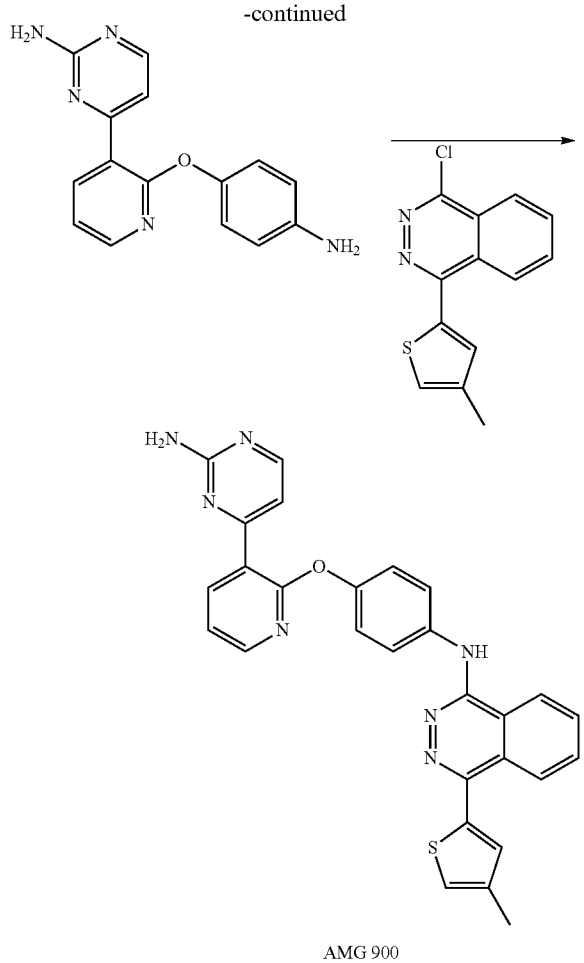

AMG 900

Synthesis of N-(4-((3-(2-amino-4-pyrimidinyl)-2-pyridinyl)oxy)phenyl)-4-(4-methyl-2-thienyl)-1-phthalazinamine (AMG 900)

Step 1: 4-(2-chloropyridin-3-yl)pyrimidin-2-amine

In an argon purged 500 mL round bottom flask placed in an isopropanol bath, was added sodium metal (3.40 g, 148 mmol) slowly to methanol (180 mL). The mixture was stirred at room temperature (RT) for about 30 minutes. To this was added guanidine hydrochloride (12.0 mL, 182 mmol) and the mixture was stirred at RT for 30 minutes, followed by addition of (E)-1-(2-chloropyridin-3-yl)-3-(dimethylamino)prop-2-en-1-one (12.0 g, 57.0 mmol), attached air condenser, moved reaction to an oil bath, where it was heated to about 50° C. for 24 h. Approximately half of the methanol was evaporated under reduced pressure and the solids were filtered under vacuum, then washed with saturated sodium bicarbonate ($NaHCO_3$) and $H_2O$, air dried to yield 4-(2-chloropyridin-3-yl)pyrimidin-2-amine as off white solid. MS m/z=207 [M+1]$^+$. Calc'd for $C_9H_7ClN_4$: 206.63.

Step 2: 4-(2-(4-aminophenoxy)pyridin-3-yl)pyrimidin-2-amine

To a resealable tube was added 4-aminophenol (1.3 g, 12 mmol), cesium carbonate (7.8 g, 24 mmol), and DMSO (16 ml, 0.75 M). The mixture was heated to 100° C. for 5 minutes, and then 4-(2-chloropyridin-3-yl)pyrimidin-2-amine (2.5 g, 12 mmol) was added, and the reaction mixture was heated to 130° C. overnight. Upon completion, as judged by LCMS, the reaction mixture was allowed to cool to RT and diluted with water. The resulting precipitate was filtered, and the solid washed with water and diethyl ether. The solid was then taken up in 9:1 $CH_2Cl_2$:MeOH and passed through a pad of silica gel with 9:1 $CH_2Cl_2$:MeOH as eluent. The solvent was concentrated in vacuo to provide the desired product, 4-(2-(4-aminophenoxy)pyridin-3-yl)pyrimidin-2-amine MS m/z=280 [M+1]$^+$. Calc'd for $C_{15}H_{13}N_5O$: 279.30.

Step 3: 1-Chloro-4-(4-methylthiophen-2-yl)phthalazine 1,4-Dichlorophthalazine (1.40 g, 7.03 mmol), 4-methylthiophen-2-ylboronic acid (999 mg, 7.03 mmol), and $PdCl_2$(DPPF) (721 mg, 985 µmol) were added into a sealed tube. The tube was purged with Argon. Then sodium carbonate (2.0 M in water) (7.74 ml, 15.5 mmol) and 1,4-dioxane (35.2 ml, 7.03 mmol) were added. The tube was sealed, stirred at RT for 5 min, and placed in a preheated oil bath at 110° C. After 1 h, LC-MS showed product and byproduct (double coupling), and starting material dichlorophthalazine. The reaction was cooled to RT, filtered through a pad of celite with an aid of ethyl acetate (EtOAc), concentrated, and loaded onto column. The product was purified by column chromatography using Hex to remove the top spot, then 80:20 hexanes:EtOAc to collect the product. The product, 1-chloro-4-(4-methylthiophen-2-yl)phthalazine was obtained as yellow solid. LC-MS showed that the product was contaminated with a small amount of dichlorophthalazine and biscoupling byproduct. MS m/z=261 [M+1]$^+$. Calcd for $C_{13}H_9ClN_2S$: 260.12.

Step 4: N-(4-((3-(2-amino-4-pyrimidinyl)oxy)phenyl)-4-(4-methyl-2-thienyl)-1-phthalazinamine To 4-(2-(4-aminophenoxy)pyridin-3-yl)pyrimidin-2-amine and 1-chloro-4-(4-methyl-2-thienyl)phthalazine was added tBuOH. The resulting mixture was heated at 100° C. in a sealed tube for 16 hours. The reaction was diluted with diethyl ether and saturated sodium carbonate and vigorously shaken. The resulting solids were filtered and washed with water, diethyl ether and air dried to yield N-(4-((3-(2-amino-4-pyrimidinyl)-2-pyridinyl)oxy)phenyl)-4-(4-methyl-2-thienyl)-1-phthalazinamine as an off-white solid. MS m/z=504 [M+H]$^+$. Calc'd for $C_{28}H_{21}N_7OS$: 503.58.

LC-MS Method:

Samples were run on a Agilent model-1100 LC-MSD system with an Agilent Technologies XDB-$C_8$ (3.5µ) reverse phase column (4.6×75 mm) at 30° C. The flow rate was constant and ranged from about 0.75 mL/min to about 1.0 mL/min.

The mobile phase used a mixture of solvent A ($H_2O$/0.1% HOAc) and solvent B (AcCN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Other methods may also be used to synthesize AMG 900. Many synthetic chemistry transformations, as well as protecting group methodologies, useful in synthesizing AMG 900, are known in the art. Useful organic chemical transformation literature includes, for example, R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

AMG 900 was tested for its ability to reduce or inhibit tumor progression in various cell lines (in-vitro) and multiple solid tumor types (in-vivo), some of which have previously been exposed to and developed resistance to standard-of-care antimitotic agents, including taxanes and vinca alkaloids, as well as to other chemotherapeutic agents. The following Example, the figures and resulting data will illustrate the ability and/or potential of AMG 900 alone, or when used in combination with other anti-cancer agents such as a chemotherapeutic agent or an HDAC inhibiting agent, to treat cancer.

Example 2

To investigate and evaluate the safety, tolerability, pharmacokinetics (pK) and pharmacodynamics (PD effect) of AMG 900 in humans, a phase I clinical dose escalation trial was conducted in patients with advanced solid tumors, wherein AMG 900 was orally dosed to the patients. Some of the objectives for the study included (1) determination of the maximal tolerated dose (MTD) and if necessary, the MTD in conjunction with prophylactic amounts of granulocyte colony stimulating factor (GCSF); (2) to evaluate the PD effects of drug exposure on phospho-histone H3 (serine 10) proteins levels in tumor tissue; (3) to evaluate change in tumor volume by volumetric or MRI analysis; and (4) to evaluate tumor response assessed by CT or MRI using RECIST criteria. The clinical trial was conducted in accordance with the following design/protocol:

Study Design

This is an open-label, sequential dose escalation study evaluating AMG 900 in subjects with advanced solid tumors. The study is being conducted in 2 parts: Part 1—Dose Escalation and Part 2—Dose Expansion. For eligible subjects in part 1 and part 2, AMG 900 will be administered daily for 4 days every 2 weeks (i.e., 4 consecutive days of dosing followed by 10 consecutive days off treatment). One cycle is defined as 14 days. Thus, 1 cycle=2 weeks (14 days) and DLT window=4 weeks (28 days).

Part 1—Dose Escalation

The dose escalation part of the study was aimed at determining a maximum tolerated dose (MTD) and if necessary the MTD with prophylactic GCSF support (MTD-G), and evaluating the safety, tolerability, pharmacokinetics and pharmacodynamics of AMG 900 in subjects with advanced solid tumors.

The dose escalation phase consisted of an initial accelerated phase (IAP; 100% dose escalation with 1 subject per cohort) until dose limiting toxicity (DLT) or grade 2 toxicity in the first 2 treatment cycles deemed to be at least possibly related to AMG 900 occurred. A subsequent non-accelerated phase (SNAP) then commenced (≤50% dose escalations once the first grade 2 related toxicity occurred; ≤25% if a DLT occurs) in a standard 3+3 design at the dose level where DLT or possibly related grade 2 toxicity was observed. The percent of dose escalation depended upon toxicities observed in previous cohorts. Intra-subject dose escalation was not allowed. An MTD was determined without prophylactic GCSF support. If neutropenia (or neutropenia related toxicity) was dose limiting, then dose escalation proceeded with prophylactic GCSF support beginning at the dose level at which neutropenia (or neutropenia related toxicity) was dose limiting. AMG 900 single dose escalation schematic is shown below:

| Cohort | Number of Subjects | Dose Escalation | Flat Dose | |
|---|---|---|---|---|
| 1 | 1 | — | 1 mg | Initial |
| 2 | 1 | 100% | 2 mg | Accelerated |
| 3 | 1 | 100% | 4 mg | Phase (IAP) |
| 4 | 1 | 100% | 8 mg | |
| 5 | 1 + 2 (if related grade 2 toxicity) OR 1 + 5 (if DLT) | ~100% | 16 mg | Subsequent Non-Accelerated Phase (SNAP) |
| 6 | 3-6 | 47% | 24 mg | |
| 7 | 3-6 | 45% | 30 mg | |
| 7a | 3-6 | | 30 mg + GCSF | |
| 7b | 3-6 | | 35 mg + GCSF | |
| 8 | 3-6 | 25% | 40 mg | |
| 9 | 3-6 | 25% | 50 mg | |

Escalation Schema*

*intermediate dose level(s) may be evaluated as necessary; six to nine subjects will be enrolled at the MTD and MTD-G; evidence of first grade 2 related toxicity noted in cohort 5 in this example - for example, see rows 7a and 7b.

Part 2—Dose Expansion

The dose expansion phase will begin after completion of the dose escalation phase and will consist of 3 cohorts of 14 subjects each. One taxane-resistant tumor type (as described in the inclusion criteria) will be evaluated in each of these cohorts: ovarian cancer, breast cancer and CRPC (other tumor types may be considered based upon preliminary results from the dose escalation phase). The dose to be evaluated will be based upon results from the dose escalation phase.

Primary and Secondary Endpoints

Primary Endpoints

Safety: subject incidence of adverse events, DLTs and clinically significant changes in vital signs, weight, ECGs and clinical laboratory tests PK profile: AMG 900 PK parameters including, but not limited to, maximum observed concentration ($C_{max}$), minimum observed concentration ($C_{min}$), area under the plasma concentration-time curve (AUC) and, if feasible, half-life ($t_{1/2,z}$)

Change in levels of p-Histone H3 from baseline (part 1—dose escalation only)

Response rate in each taxane-resistant tumor type (ovarian, triple-negative breast and CRPC) assessed per RECIST guidelines (part 2—dose expansion only), as well as by CA-125 in ovarian cancer subjects by Rustin criteria, and by PSA in CRPC subjects by PCWG2 guidelines.

Secondary Endpoints

Change in tumor volume from baseline measured by volumetric CT or MRI

Tumor response measured by CT or MRI and assessed per RECIST guidelines, as well as per Rustin Criteria in ovarian tumors, and per PCWG2 criteria in CRPC Change from baseline in maximum standardized uptake value ($SUV_{max}$) using $^{18}$FLT-PET/CT (part 2—dose expansion only)

Exploratory Endpoints

PK/PD relationships

Relation between change in tumor volume and change in $SUV_{max}$,

Levels of several tumor biomarkers (such as levels of p53, p21, aurora A and B DNA and mRNA, survivin mRNA and status of p53)

AMG 900 Dosage and Administration

AMG 900 was provided as an orally administrable dosage formulation. A diary was provided for subjects to record their adherence to the oral medication.

For eligible subjects in part 1 and part 2, AMG 900 was administered daily for 4 days every 2 weeks (i.e., 4 consecutive days of dosing followed by 10 consecutive days off treatment). For once daily (QD) dosing, subjects self-administered AMG 900 on an empty stomach in the morning (no food or liquids except water 2 hours prior to drug) and refrain from food and liquid (except water) intake for 1 hour post-dose. In addition, treatment with proton pump inhibitors or H2 receptor antagonists was withheld at least 48 hours prior to the first dose of each treatment cycle until at least 1 hour after the fourth dose of a treatment cycle.

Starting Dose:

The first cohort self-administered 1 mg of AMG 900 QD in the morning. The subject was monitored in the clinic for at least 2 hours for any signs of adverse events. For cohorts evaluated with prophylactic GCSF support as a result of dose limiting neutropenia, GCSF was given subcutaneously every day starting at least 24 hours after the last dose of AMG 900 in a treatment cycle and continued until ANC is at least 1000, in accordance with standard prescribing guidelines.

Control Group: None

Procedures

Subjects were considered enrolled on study day 1 when AMG 900 was first administered. AMG 900 was administered daily for 4 days every 2 weeks (i.e., 4 consecutive days of dosing, followed by 10 consecutive days off treatment). Subjects self-administered AMG 900 on an empty stomach in the morning (no food or liquids except water 2 hours prior to dosing) and refrained from food or liquids except water for 1 hour post-dose. In addition, treatment with proton pump inhibitors or H2 receptor antagonists were withheld at least 48 hours prior to the first dose of each treatment cycle until at least 1 hour after the fourth dose of a treatment cycle. One cycle was defined as 14 days. Subjects were seen in clinic weekly for the first 9 weeks and every cycle thereafter for their study visits. The investigator or sub-investigator performed a physical examination of each subject during clinic visits. A review of concomitant medications and an assessment of adverse events were performed at every visit.

Efficacy was assessed by standardized contrast-enhanced CT or MRI and evaluated according to RECIST criteria. RECIST 1.0 and RECIST 1.1 criteria is described in the *Journal of National Cancer Institute*, Vol. 92, No. 3:205-216, 2000 and *European Journal of Cancer* 45:228-247, 2009, respectively, both disclosures of which are hereby incorporated herein by reference in their entireties. CT or MRI scans with contrast were acquired at baseline, 4 weeks after cycle 1 day 1, 8 weeks after cycle 1 day 1, and every 8 weeks thereafter until disease progression. Scans were acquired with slice thickness of about 5 mm or less. Baseline imaging studies were performed within 2 weeks prior to study day 1, and where practicable, they were performed as close to the day of enrollment as possible.

Disease progression by appearance of new bone lesions in CRPC in the dose expansion phase were evaluated with bone scans. Bone scans were performed at baseline, 4 weeks after cycle 1 day 1, 8 weeks after cycle 1 day 1, and every 8 weeks thereafter until disease progression. Efficacy in ovarian cancer and CRPC were evaluated based on the Rustin criteria (1996) and PCWG2 guidelines, respectively. CA-125 in ovarian cancer and PSA in CRPC were collected every 4 weeks.

[18]FLT-PET/CT scans are being performed for all subjects enrolled in the dose expansion phase to measure tumor proliferative response after treatment. The procedure is being performed at baseline and cycle 1 day 5. Scans are being submitted to the imaging core laboratory for assessment of maximum and mean standardized uptake value ($SUV_{max}$ and $SUV_{mean}$). All scans are being done with contrast agent as indicated in the Imaging Manual provided by the core laboratory. All subsequent scans are being performed in the same manner as at baseline, preferably on the same scanner. Scans were are are being submitted to an independent imaging core laboratory for assessment of volumetric CT or MRI. Determination of disease progression for clinical management of subjects on study were and are being assessed at the local site. Where necessary, subjects in the subsequent non-accelerated phase (SNAP) of the dose escalation cohorts underwent matched fine needle aspirations (FNA) of a single site of tumor deposit within 7 days prior to their first dose of AMG 900 and 3-6 hours after the first dose on cycle 1 day 1.

Statistical Considerations

The primary analysis for this study occurred after all subjects have either completed the study or completed 9 months of treatment. Subjects who were still active at the time of the primary analysis were allowed to continue on study until disease progression or medication intolerance was observed.

Tumor Response Results

AMG 900 has exhibited positive responses in various solid tumor types in the human Ph I clinical trial at doses prescribed in accordance with the "on-off" dosage schedule described above.

As shown in FIGS. 1-*a*, 1-*b*, 2-*a*, 2-*b*, 3-*a*, 3-*b*, 4-*a*, 4-*b*, 5-*a* and 5-*b*, AMG 900 displayed a surprising property of being able to reduce or decrease the physical size of a solid tumor in both the ovary as well as in the endometrial lining of the uterus wall. This anti cancer activity was observed with low dosages of AMG 900, as low as a once daily 8 mg dose. Importantly, MTD's and DLT's were not observed until doses of AMG 900 were much greater than 8 mg, thus allowing higher doses of AMG 900 and/or varied dosage regimens to provide meaningful and significant anti-cancer benefits to patients.

As shown in FIGS. 1-*a* and 1-*b*, and particularly illustrated in FIG. 1-*b*, an AMG 900 dosage regiment comprising of dosing AMG 900 at a dose of about 30 mg once daily for four (4) consecutive days ("on" treatment) and then non-treatment for 10 consecutive days ("off" treatment), followed by "on" once daily treatment again for four (4) consecutive days followed again by "off" treatment for 10 consecutive days, and so on and so off for 24 weeks, had a positive response in a patient with advanced solid endometrial cancerous tumor at week no. 24. Specifically, FIG. 1-*a* illustrates diametric measurements along the long axis of the tumor dosed with 30 mg+GCSF once daily over a period of two (12) cycles, i.e., 24 weeks (168 days). The figure reveals, as measured by CT and calculated using RECIST 1.0, that the long axis diameter was decreased by approximately 50% at week 24 (see FIG. 1-*b*) versus the base line diameter of the same tumor on day 1. This is clear evidence of clinical benefit of AMG 900 at dose of 30 mg over a specified dosing regimen.

FIGS. 2-*a* and 2-*b* confirm the finding of FIGS. 1-*a* and 1-*b*. FIGS. 2-*a* and 2-*b* are measurements of the same endometrial solid tumor depicted in FIGS. 1-*a* and 1-*b*, but with its size shown as measured alone the short axis by CT and calculated using RECIST 1.1. As shown in FIG. 1-*b*, the short axis diameter at week 16 was reduced by up to 40% after eight (8) cycles of treatment with 30 mg once daily dose of AMG 900.

As shown in FIGS. 3-*a* and 3-*b*, and particularly illustrated in FIG. 3-*b*, an AMG 900 dosage regiment comprising of dosing AMG 900 at a dose ranging from about 16 mg to about 30 mg once daily for four (4) consecutive days ("on" treatment) and then non-treatment for 10 consecutive days ("off" treatment), followed by "on" once daily treatment again for four (4) consecutive days followed again by "off" treatment for 10 consecutive days, and so on and so off, had a positive response in a patient with advanced solid ovarian cancerous tumor at week no. 4. Specifically, FIG. 3-a illustrates diametric measurements along the short axis of the tumor dosed with 30 mg once daily over a period of two (2) cycles, i.e., 4 week (28 days). The figure reveal, as measured by RECIST 1.1, that the short axis diameter had reduced by approximately 30% (see FIG. 3-b) versus the base line diameter of the same tumor on day 1. This is clear evidence of clinical benefit of AMG 900 at 30 mg.

FIGS. 4-a and 4-b confirm the finding of FIGS. 3-a and 3-b. FIGS. 4-a and 4-b are measurements of the same ovarian tumor depicted in FIGS. 3-a and 3-b, but with its size shown as measured alone the long axis by RECIST 1.0. As shown in FIG. 4-b, the long axis diameter at week 4 had reduced by between 30 and 35% after two (2) cycles of treatment with 30 mg once daily doses of AMG 900.

FIGS. 5-a and 5-b illustrate that other membranes and linings of the subject's ovarian tumors also exhibited positive responses with 4-day on-10 day off, 2-cycle treatment with AMG 900 at a once daily dose of 30 mg/kg. More specifically, the cancerous portions of the vaginal cuff, para-aortic and diaphragm areas of the uterus decreased from about 10% to about 25% when compared with base line.

Further to substantiate the positive effects of AMG 900 on ovarian cancer, a 66-year old platinum-sensitive ovarian cancer patient, who had 3 prior platinum treatment regimens (last PFS, 21 months) and had cyclical grade 4 neutropenia, was dosed AMG 900 at 16 mg once daily pursuant the 4-day on-10 day off regimen/cycle described above. The once daily dose was reduced to 8 mg for cycles 4-15, then increased to 12 mg at cycle 16. At the end of cycle 16, the tumor exhibited a positive response with a 16% decrease in SLD (sum of long axis diameters) on CT and a 45% decrease in CA-125. This further verifies the positive effects of AMG 900, when dosed according to a specified cycle, on solid cancerous tumors.

Additional cancer subjects of the first-in-human Ph I trial were treated with AMG 900 in accordance with the dose escalation schedule protocol and the dosage cycle described above, and exhibited results wherein the tumors were stabilized. More specifically, patients having gastroesophogeal cancer, lung cancer, breast cancer, colon cancer, paraganglioma and medullary thyroid cancer, each in the form of an advanced solid tumor, all exhibited stabilization in growth of the tumors and/or decreases in size ranging from about 5% to about 10% of the tumor. The sizes were measured, and decreases determined, by the methods described herein. This is further evidence of the use of AMG 900 in treating various forms of cancer.

Indications

AMG 900 is a pan aurora kinase inhibitor. Aurora kinase proteins play a part in cell cycling and, therefore, cell proliferation. Aurora kinases are enzymes of the serine/threonine kinase family of proteins, which play an important role in protein phosphorylation during the mitotic phase of the cell cycle. There are three known members of the Aurora kinase family, Aurora A, Aurora B and Aurora C, also referred to as Aurora 2, Aurora 1, and Aurora 3, respectively.

Specifically, the function of each Aurora kinase isoform in mammalian cell cycle has been studied. Aurora-A is localized to the centrosome during interphase and is important for centrosome maturation and to maintain separation during spindle assembly. Aurora-B localizes to the kinetochore in the G2 phase of the cell cycle until metaphase, and relocates to the midbody after anaphase. Aurora-C was thought to function only in meiosis, but more recently has been found to be more closely related to Aurora-B, showing some overlapping functions and similar localization patterns in mitosis. Each aurora kinase appears to share a common structure, including a highly conserved catalytic domain and a very short N-terminal domain that varies in size. (See R. Giet and C. Prigent, J. Cell. Sci., 112:3591-3601 (1999)).

Aurora kinases are over expressed in various types of cancers, including colon, breast, lung, pancreas, prostate, bladder, kidney, thyroid, esophageal, gastric, head, neck, cervix, uterus, and ovarian cancers. The Aurora-A gene is part of an amplicon found in a subset of breast, colon, ovarian, liver, gastric and pancreatic tumors. Aurora-B has also been found to be over expressed in most major tumor types. Over expression of Aurora-B in rodent fibroblasts induces transformation, suggesting that Aurora-B is oncogenic. More recently, Aurora-B mRNA expression has been linked to chromosomal instability in human breast cancer. (Y. Miyoshi et al., Int. J. Cancer, 92:370-373 (2001)).

AMG 900 has responses in various tumor types ranging from disease stabilization (that is suppresses or arrests the growth and increase in size of the tumor) to positive response (that is it inhibited tumor growth or caused actual tumor shrinkage) on solid tumors. For instance, the following represents some of the data available for AMG 900 in a Ph I dose escalation study in humans, where patients 1-15 (1-13 were in the solid tumor study) was dosed AMG 900 orally in the dosage amount indicated once daily for 4 consecutive days and not dosed with AMG 900 for 10 consecutive days (one dosage regimen cycle). Patient 16 in the AML study had a dosage regimen of 7 consecutive days on AMG 900 and 7 consecutive days off. The data for both studies are as follows:

| Patient No. | Dose Level (mg once per day) | Tumor Type | Days on Study | Observed Response to AMG 900 |
|---|---|---|---|---|
| 1 | 1 | cholangiocarcinoma | 199 | SD at week 24 |
| 2 | 8 | prostate | 148 | SD at week 8 |
| 3 | 16 | ovarian | 339 | SD at week 40 |
| 4 | 16 | breast | 79 | SD at week 4 |
| 5 | 24 | colon | 134 | SD at week 8 |
| 6 | 25 | rectal | 463 | PD at week 56 |
| 7 | 24 | Medullary thyroid | 875 | SD at week 120 |
| 8 | 30 + GCSF | endometrial | 547 | PR at Week 64; SD at week 72 |
| 9 | 30 + GCSF | chondrosarcoma | 350 | SD at week 40 |
| 10 | 40 + GCSF | colon | 231 | SD at week 32 |
| 11 | 40 + GCSF | Non-small cell lung | 281 | SD at week 32 |
| 12 | 50 + GCSF | thyroid | 267 | SD at week 32 |
| 13 | 40 + GCSF | prostate | 83 | SD at week 8 |
| 14 | 80 | AML | 81 | Active |
| 15 | 80 | AML | 38 | Active |
| 16 | 30 | AML | 10 | Active |

KEY: SD means stable disease, indicating that the patient's progressing tumor actually stabilized during the time period dosed with AMG 900 at the dosage amount indicated. Similarly, PD means partial disease, ie., it progressed but not as fast as without AMG 900. PR means partial response, indicating that the patient's progressing tumor actually decreased or reduced in size during the time period dosed with AMG 900 at the dosage amount indicated.

The present invention provides a method of treating cancer in a subject comprising administering to the subject a dosage regimen comprising a once daily dose of AMG 900, or a pharmaceutically acceptable salt thereof, ranging from about 1 mg to about 50 mg (embodiment 1).

In embodiment 2, the invention provides the method of embodiment 1, wherein the dosage regimen comprises orally administering the once daily dose of AMG 900 to the subject for 3, 4, 5, 6, 7, 8, 9 or 10 consecutive days.

In embodiment 3, the invention provides the method of any one of embodiments 1 and 2, wherein the dosage regimen comprises orally administering the once daily dose of AMG 900 to the subject for 3, 4, 5, 6 or 7 consecutive days.

In embodiment 4, the invention provides the method of any one of embodiments 1-3, wherein the dosage regimen comprises orally administering the once daily dose of AMG 900 to the subject for 4, 5, 6 or 7 consecutive days.

In embodiment 5, the invention provides the method of any one of embodiments 1-4, wherein the dosage regimen comprises orally administering the once daily dose of AMG 900 to the subject for 4 consecutive days.

In embodiment 6, the invention provides the method of any one of embodiments 1-4, wherein the dosage regimen comprises orally administering the once daily dose of AMG 900 to the subject for 7 consecutive days.

In embodiment 7, the invention provides the method of any one of embodiments 1-6, wherein the dosage regimen further comprises non-treatment of AMG 900 for a period ranging from 6 to 20 consecutive days immediately following the once daily consecutive day treatment of AMG 900.

In embodiment 8, the invention provides the method of any one of embodiments 1-7, wherein the dosage regimen further comprises non-treatment of AMG 900 for a period ranging from 10 to 20 consecutive days immediately following the once daily consecutive day treatment of AMG 900.

In embodiment 9, the invention provides the method of any one of embodiments 1-8, wherein the dosage regimen further comprises non-treatment of AMG 900 for a period ranging from 10 to 12 consecutive days immediately following the once daily consecutive day treatment of AMG 900.

In embodiment 10, the invention provides the method of any one of embodiments 1-9, wherein the dosage regimen further comprises non-treatment of AMG 900 for a period of 10 consecutive days immediately following the once daily consecutive day treatment of AMG 900.

In embodiment 11, the invention provides the method of any one of embodiments 1-10, wherein the dosage regimen comprises orally administering the once daily dose of AMG 900 to the subject for 4, 5, 6 or 7 consecutive days followed immediately by non-treatment of AMG 900 for a period ranging from 6 to 20 consecutive days.

In embodiment 12, the invention provides the method of any one of embodiments 1-11, wherein the dosage regimen comprises orally administering the once daily dose of AMG 900 to the subject for 4 or 7 consecutive days followed immediately by non-treatment of AMG 900 for a period ranging from 6 to 15 consecutive days.

In embodiment 13, the invention provides the method of any one of embodiments 1-12, wherein the dosage regimen comprises orally administering the once daily dose of AMG 900 to the subject for 4 consecutive days followed immediately by non-treatment of AMG 900 for a period of 10 consecutive days.

In embodiment 14, the invention provides the method of any one of embodiments 1-13, wherein the dosage regimen comprises orally administering AMG 900 to the subject in a once daily dose or dosage amount ranging from about 8 mg to about 40 mg for 4 consecutive days followed immediately by non-treatment of AMG 900 for a period of 10 consecutive days.

In embodiment 15, the invention provides the method of any one of embodiments 1-14, wherein the dosage regimen comprises orally administering AMG 900 to the subject in a once daily dose or dosage amount ranging from about 16 mg to about 40 mg for 4 consecutive days followed immediately by non-treatment of AMG 900 for a period of 10 consecutive days.

In embodiment 16, the invention provides the method of any one of embodiments 1-15, wherein the dosage regimen comprises orally administering AMG 900 to the subject in a once daily dose ranging from about 16 mg to about 30 mg for 4 consecutive days followed immediately by non-treatment of AMG 900 for a period of 10 consecutive days.

In embodiment 17, the invention provides the method of any one of embodiments 1-16 wherein the cancer is one or more of (a) a solid or hematologically derived tumor selected from (a) cancer of the bladder, breast, colon, kidney, liver, lung, small cell lung cancer, esophagus, gall-bladder, ovary, endometrium, pancreas, stomach, uterus, cervix, thyroid, brain, prostate and skin, (b) a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma, (c) a hematopoietic tumor of myeloid lineage selected from acute and chronic myelogenous leukemias, myelodysplastic syndrome and promyelocytic leukemia (d) a tumor of mesenchymal origin selected from fibrosarcoma and rhabdomyosarcoma, (e) a tumor of the central and peripheral nervous system selected from astrocytoma, neuroblastoma, glioma and schwannoma, and (f) a melanoma, seminoma, teratocarcinoma, osteosarcoma, xenoderoma pigmentosum, keratoctanthoma, thyroid follicular cancer or Kaposi's sarcoma.

In embodiment 18, the invention provides the method of any one of embodiments 1-17 wherein the cancer is one or more of a solid tumor selected from cancer of the bladder, breast, colon, kidney, liver, lung, non-small cell lung, head and neck, esophageal, gastric, ovary, endometrium, pancreas, stomach, uterus, cervix, thyroid, brain and prostate or a lymphoma or leukemia, or a combination thereof.

In embodiment 19, the invention provides the method of any one of embodiments 1-17 wherein the cancer is a solid cancer tumor of the prostate, ovary, endometrium, breast, bladder, colon, kidney, liver, lung, esophagus, pancreas, stomach, uterus, cervix, thyroid, brain or skin, or a combination thereof.

In embodiment 20, the invention provides the method of any one of embodiments 1-19 wherein the dosage amount of AMG 900, or a pharmaceutically acceptable salt thereof, is in the range of about 1.5 mg to about 45 mg.

In embodiment 21, the invention provides the method of any one of embodiments 1-20 wherein the dosage amount of AMG 900 or a pharmaceutically acceptable salt thereof, is in the range of about 5 mg to about 45 mg.

In embodiment 22, the invention provides the method of any one of embodiments 1-21 wherein the dosage amount of AMG 900 or a pharmaceutically acceptable salt thereof, is in the range of about 10 mg to about 40 mg.

In embodiment 22, the invention provides the method of any one of embodiments 1-22 wherein the dosage amount of AMG 900 or a pharmaceutically acceptable salt thereof, is in the range of about 15 mg to about 40 mg.

In embodiment 24, the invention provides the method of any one of embodiments 1-23 wherein the dosage amount of AMG 900 or a pharmaceutically acceptable salt thereof, is in the range of about 16 mg to about 35 mg.

In embodiment 25, the invention provides the method of slowing the rate of growth of a solid tumor in a subject, the method comprising administering AMG 900, or a pharmaceutically acceptable salt thereof, to the subject in a dosage regimen comprising a dose of AMG 900 ranging from about 10 mg to about 45 mg.

In embodiment 26, the invention provides the method of any one of embodiments 1-24 wherein the dosage regimen comprises administering AMG 900, or a pharmaceutically acceptable salt thereof, in combination with a second anti-cancer agent.

In embodiment 27, the invention provides the method of embodiment 26 wherein the second anti-cancer agent is an HDAC inhibiting agent.

In embodiment 28, the invention provides the method of embodiment 27 wherein AMG 900 and the HDAC inhibiting agent are administered sequentially or co-administered simultaneously.

In embodiment 29, the invention provides the method of any one of embodiments 16-28 wherein the AMG 900, or a pharmaceutically acceptable salt thereof, and the HDAC inhibiting agent are co-administered in a single dosage formulation.

In embodiment 30, the invention provides the method of any one of embodiments 16-29 wherein the AMG 900, or a pharmaceutically acceptable salt thereof, and the HDAC inhibiting agent are co-administered as separate dosage formulations.

In embodiment 31, the invention provides the method of any one of embodiments 27-30 wherein the HDAC inhibiting agent is Vorinostat, Romidepsin, Panobinostat (LBH589), valproic acid, Belinostat (PXD101), Mocetinostat (MGCD103), Abexinostat (PCI-24781), Entinostat (MS-275), SB939, Resminostat (4SC-210), Givinostat (ITF2357), CUDC-101, AR-42, CHR-2845, CHR-3996, 4SC-202, CG200745, ACY-1215 or Sulforphane.

In embodiment 32, the invention provides the method of any one of embodiments 1-17 wherein the dosage regimen comprises administering AMG 900, or a pharmaceutically acceptable salt thereof, in combination with GCSF.

In embodiment 34, the invention provides the method of any one of embodiments 1-32 wherein the dosage regimen further comprises administering GCSF in an amount ranging from about 5 mcg/kg to about 200 mcg/kg by weight of the subject.

In embodiment 35, the invention provides the method of any one of embodiments 1-34 wherein the subject is a human.

In embodiment 36, the invention provides the method of embodiment 26 wherein the second anti-cancer agent is selected from methotrexate; tamoxifen; fluorouracil; 5-fluorouracil; hydroxyurea; mercaptopurine; cisplatin; carboplatin; daunorubicin; doxorubicin; etoposide; vinblastine; vincristine; paclitaxel; thioguanine; idarubicin; dactinomycin; imatinib; gemcitabine; altretamine; asparaginase; bleomycin; capecitabine; carmustine; cladibrine; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant and nelarabine, or a combination thereof.

Administering AMG 900 to a subject may be optimal if done so on an empty stomach. Thus, and as provided herein, embodiment 37 of the present invention further provides use of AMG 900 to treat cancer wherein the dosage regimen of any of embodiments 1-36 further comprises administering to the subject AMG 900, or a pharmaceutically acceptable salt thereof, to the subject at a time when the subject has not eaten food for a minimum of one hour immediately prior to administering the dose of AMG 900.

In embodiment 38, the dosage regimen of any one of embodiments 1-37 herein above may further comprise fasting the subject for at least one hour after administering the dose of AMG 900, or a pharmaceutically acceptable salt thereof, to the subject.

In embodiment 39, the dosage regimen of any one of embodiments 1-38 herein above may comprise fasting the subject for at least one hour immediately prior to and immediately after administering the dose of AMG 900, or a pharmaceutically acceptable salt thereof, to the subject.

In embodiment 40, the invention provides the method of any one of embodiments 1-15, wherein the dosage regimen comprises orally administering AMG 900 to the subject in a once daily dose ranging from about 20 mg to about 30 mg for 4 consecutive days followed immediately by non-treatment of AMG 900 for a period of 10 consecutive days.

In embodiment 41, the invention provides the method of any one of embodiments 1-15, wherein the dosage regimen comprises orally administering AMG 900 to the subject in a once daily dose ranging from about 20 mg to about 25 mg for 4 consecutive days followed immediately by non-treatment of AMG 900 for a period of 10 consecutive days.

In embodiment 42, the invention provides the method of any one of embodiments 1-15, wherein the dosage regimen comprises orally administering AMG 900 to the subject in a once daily dosage amount ranging from about 24 mg to about 25 mg for 4 consecutive days followed immediately by non-treatment of AMG 900 for a period of 10 consecutive days.

In embodiment 43, the invention provides the method of any one of embodiments 1-16 wherein the cancer is (a) a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma or (b) a hematopoietic tumor of myeloid lineage selected from acute and chronic myelogenous leukemias, myelodysplastic syndrome and promyelocytic leukemia.

In embodiment 44, the invention provides the method of any one of embodiments 17-19, wherein the dosage regimen comprises orally administering AMG 900 to the subject in a once daily dose ranging from about 20 mg to about 30 mg for 4 consecutive days followed immediately by non-treatment of AMG 900 for a period of 10 consecutive days.

In embodiment 45, the invention provides the method of any one of embodiments 17-19, wherein the dosage regimen comprises orally administering AMG 900 to the subject in a once daily dose ranging from about 20 mg to about 25 mg for 4 consecutive days followed immediately by non-treatment of AMG 900 for a period of 10 consecutive days.

In embodiment 46, the invention provides the method of any one of embodiments 17-19, wherein the dosage regimen comprises orally administering AMG 900 to the subject in a once daily dosage amount ranging from about 24 mg to about 25 mg for 4 consecutive days followed immediately by non-treatment of AMG 900 for a period of 10 consecutive days.

In embodiment 47, the invention provides the method of any one of embodiments 17 and 43, wherein the dosage regimen comprises orally administering AMG 900 to the subject in a once daily dose ranging from about 10 mg to about 80 mg for 7 consecutive days followed immediately by non-treatment of AMG 900 for a period of 7 consecutive days.

In embodiment 48, the invention provides the method of any one of embodiments 17 and 43, wherein the dosage regimen comprises orally administering AMG 900 to the subject in a once daily dose ranging from about 20 mg to about 40 mg for 7 consecutive days followed immediately by non-treatment of AMG 900 for a period of 7 consecutive days.

In embodiment 49, the invention provides the method of any one of embodiments 17 and 43, wherein the dosage regimen comprises orally administering AMG 900 to the subject in a once daily dosage amount ranging from about 25 mg to about 35 mg for 7 consecutive days followed immediately by non-treatment of AMG 900 for a period of 7 consecutive days.

In embodiment 50, the invention provides use of AMG 900, or a pharmaceutically acceptable salt thereof, to treat cancer in a human, wherein AMG 900, or a pharmaceutically acceptable salt thereof, is administered to the human in a dosage regimen comprising a once daily dose ranging from about 5 mg to about 80 mg.

In embodiment 51, the invention provides use of embodiment 50, wherein AMG 900, or a pharmaceutically acceptable salt thereof, is administered in a once daily dose ranging from about 5 mg to about 45 mg.

In embodiment 52, the invention provides use of any one of embodiments 50-51, wherein AMG 900 is administered in a once daily dose ranging from about 10 mg to about 40 mg.

In embodiment 53, the invention provides use of any one of embodiments 50-52, wherein AMG 900, or a pharmaceutically acceptable salt thereof, is administered in a once daily dose ranging from about 16 mg to about 35 mg.

In embodiment 54, the invention provides use of any one of embodiments 50-53, wherein AMG 900, or a pharmaceutically acceptable salt thereof, is administered in a once daily dose ranging from about 20 mg to about 25 mg.

In embodiment 55, the invention provides use of any one of embodiments 50-54, wherein AMG 900, or a pharmaceutically acceptable salt thereof, is administered in a once daily dose of about 24 mg.

In embodiment 56, the invention provides use of embodiment 50, wherein AMG 900, or a pharmaceutically acceptable salt thereof, is administered in a once daily dose ranging from about 40 mg to about 80 mg.

In embodiment 57, the invention provides use of any one of embodiments 50-56, wherein the dosage regimen further comprises orally administering the dose of AMG 900, or a pharmaceutically acceptable salt thereof, to the human for 3, 4, 5, 6, 7, 8, 9 or 10 consecutive days.

In embodiment 58, the invention provides use of any one of embodiments 50-57, wherein AMG 900, or a pharmaceutically acceptable salt thereof, is orally administered to the human for 3, 4, 5, 6 or 7 consecutive days.

In embodiment 59, the invention provides use of any one of embodiments 50-58, wherein AMG 900, or a pharmaceutically acceptable salt thereof, is orally administered to the human for 4, 5, 6 or 7 consecutive days.

In embodiment 60, the invention provides use of any one of embodiments 50-59, wherein AMG 900, or a pharmaceutically acceptable salt thereof, is orally administered to the human for 4 consecutive days.

In embodiment 61, the invention provides use of any one of embodiments 50-59, wherein AMG 900, or a pharmaceutically acceptable salt thereof, is orally administered to the human for 7 consecutive days.

In embodiment 62, the invention provides use of any one of embodiments 57-61, wherein the dosage regimen further comprises non-treatment of AMG 900, or a pharmaceutically acceptable salt thereof, for a period ranging from 6 to 20 consecutive days immediately following the once daily consecutive day treatment with AMG 900.

In embodiment 63, the invention provides use of any one of embodiments 50-62, wherein AMG 900, or a pharmaceutically acceptable salt thereof, is orally administered to the human for 4, 5, 6 or 7 consecutive days followed immediately by non-treatment of AMG 900, or a pharmaceutically acceptable salt thereof, for a period ranging from 6 to 20 consecutive days.

In embodiment 64, the invention provides use of any one of embodiments 50-63, wherein AMG 900, or a pharmaceutically acceptable salt thereof, is orally administered to the human for 4 or 7 consecutive days followed immediately by non-treatment of AMG 900, or a pharmaceutically acceptable salt thereof, for a period ranging from 6 or 15 consecutive days.

In embodiment 65, the invention provides use of any one of embodiments 50-64, wherein the dosage regimen further comprises administering AMG 900, or a pharmaceutically acceptable salt thereof, in combination with GCSF.

In embodiment 66, the invention provides use of embodiment 65, wherein the GCSF is administered in an amount ranging from about 5 mcg/kg to about 200 mcg/kg by weight of the human.

In embodiment 67, the invention provides use of any one of embodiments 65-66, wherein AMG 900, or a pharmaceutically acceptable salt thereof, is administered in a once daily dose ranging from about 20 mg to about 40 mg in combination with GCSF administered in an amount ranging from about 5 mcg/kg to about 200 mcg/kg by weight of the human.

In embodiment 68, the invention provides use of any one of embodiments 65-67 wherein AMG 900, or a pharmaceutically acceptable salt thereof, is administered in a once daily dose ranging from about 30 mg to about 40 mg in combination with GCSF administered in an amount ranging from about 5 mcg/kg to about 200 mcg/kg by weight of the human.

In embodiment 69, the invention provides use of any one of embodiments 50-69, wherein the dosage regimen further comprises fasting the human for at least one hour immediately prior to administering AMG 900, or a pharmaceutically acceptable salt thereof, and for at least another 2 hours immediately after administering AMG 900, or a pharmaceutically acceptable salt thereof.

In embodiment 70, the invention provides use of any one of embodiments 50-69, wherein the cancer is one or more of (a) a solid or hematologically derived tumor selected from (a) cancer of the bladder, breast, colon, kidney, liver, lung, small cell lung cancer, esophagus, gall-bladder, ovary, endometrium, pancreas, stomach, uterus, cervix, thyroid, brain, prostate and skin, (b) a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma, (c) a hematopoietic tumor of myeloid lineage selected from acute and chronic myelogenous leukemias, myelodysplastic syndrome and promyelocytic leukemia (d) a tumor of mesenchymal origin selected from fibrosarcoma and rhabdomyosarcoma, (e) a tumor of the central and peripheral nervous system selected from astrocytoma, neuroblastoma, glioma and schwannoma, and (f) a melanoma, seminoma, teratocarcinoma, osteosarcoma, xenoderoma pigmentosum, keratoctanthoma, thyroid follicular cancer or Kaposi's sarcoma.

In embodiment 71, the invention provides use of any one of embodiments 50-69 wherein the cancer is one or more of a solid tumor selected from cancer of the bladder, breast, colon, kidney, liver, lung, non-small cell lung, head and neck, esophageal, gastric, ovary, endometrium, pancreas, stomach, uterus, cervix, thyroid, brain and prostate or a lymphoma or leukemia, or a combination thereof.

In embodiment 72, the invention provides use of any one of embodiments 50-69 wherein the cancer is a solid cancer tumor of the prostate, ovary, endometrium, breast, bladder, colon, kidney, liver, lung, esophagus, pancreas, stomach, uterus, cervix, thyroid, brain or skin, or a combination thereof.

In embodiment 73, the invention provides use of any one of embodiments 50-70 wherein the cancer is (a) a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma or (b) a hematopoietic tumor of myeloid lineage selected from acute and chronic myelogenous leukemias, myelodysplastic syndrome and promyelocytic leukemia, or a combination thereof.

In embodiment 74, the invention provides use of any one of embodiments 50-70 and 73, wherein the cancer is a hematopoietic tumor of myeloid lineage selected from acute and chronic myelogenous leukemias, myelodysplastic syndrome and promyelocytic leukemia, or a combination thereof.

In embodiment 75, the invention provides use of any one of embodiments 50-70 wherein the cancer is selected from the group consisting of prostate cancer, neuroendocrine cancer, ovarian cancer, endometrial cancer, breast cancer, uterine cancer and cervical cancer, or a combination thereof.

In embodiment 76, the invention provides use of any one of embodiments 50-75 wherein the dosage regimen comprises administering AMG 900, or a pharmaceutically acceptable salt thereof, in combination with a second anti-cancer agent.

In embodiment 77, the invention provides use of embodiment 76 wherein the second anti-cancer agent is methotrexate; tamoxifen; fluorouracil; 5-fluorouracil; hydroxyurea; mercaptopurine; cisplatin; carboplatin; daunorubicin; doxorubicin; etoposide; vinblastine; vincristine; paclitaxel; thioguanine; idarubicin; dactinomycin; imatinib; gemcitabine; altretamine; asparaginase; bleomycin; capecitabine; carmustine; cladibrine; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant or nelarabine, or a combination thereof.

In embodiment 78, the invention provides use of any one of embodiments 50-77 wherein the dosage regimen comprises fasting the human for one hour immediately prior to and for at two hours immediately after administering the once daily dose of AMG 900, or a pharmaceutically acceptable salt thereof.

In embodiment 79, the invention provides a pharmaceutical composition for treatment of cancer, the composition comprising AMG 900, or a pharmaceutically acceptable salt thereof, in an effective dosage amount ranging from about 20 mg to about 45 mg, wherein the composition is administered to a human as a once daily dosage form for either 4 consecutive days or 7 consecutive days to treat the cancer.

In embodiment 80, the invention provides a method of treating a solid tumor or leukemia in a human comprising administering to the human a dosage regimen comprising (1) a once daily dose of AMG 900, or a pharmaceutically acceptable salt thereof, ranging from about 10 mg to about 80 mg, and (2) administering the once daily dose of AMG 900 to the human in a dosing schedule comprising either (a) 4 consecutive days of treatment with AMG 900 followed by 10 consecutive days of non-treatment, or (b) 7 consecutive days of treatment with AMG 900 followed by 7 consecutive days of non-treatment, to treat the solid tumor or leukemia.

In embodiment 81, the invention provides a method of treating a solid tumor in a human comprising administering to the human a dosage regimen comprising (1) a once daily dose of AMG 900, or a pharmaceutically acceptable salt thereof, ranging from about 10 mg to about 50 mg, and (2) administering the once daily dose of AMG 900 to the human in a dosing schedule comprising 4 consecutive days of treatment with AMG 900 followed by 10 consecutive days of non-treatment, to treat the solid tumor or leukemia.

In embodiment 82, the invention provides a method of treating acute myelogenous leukemia (AML) or chronic myelogenous leukemia (CML) in a human comprising administering to the human a dosage regimen comprising (1) a once daily dose of AMG 900, or a pharmaceutically acceptable salt thereof, ranging from about 30 mg to about 120 mg, and (2) administering the once daily dose of AMG 900 to the human in a dosing schedule comprising either (a) 4 consecutive days of treatment with AMG 900 followed by 10 consecutive days of non-treatment, or (b) 7 consecutive days of treatment with AMG 900 followed by 7 consecutive days of non-treatment, to treat the solid tumor or leukemia.

In embodiment 83, the invention provides use of any one of embodiments 80-81, wherein AMG 900 is administered in a once daily dose ranging from about 20 mg to about 40 mg.

In embodiment 84, the invention provides use of any one of embodiments 80-81, wherein AMG 900, or a pharmaceutically acceptable salt thereof, is administered in a once daily dose ranging from about 24 mg to about 35 mg.

In embodiment 85, the invention provides use of any one of embodiments 82, wherein AMG 900, or a pharmaceutically acceptable salt thereof, is administered in a once daily dose ranging from about 50 mg to about 100 mg.

To this end, AMG 900 is useful for, but not limited to, the prevention or treatment of cancer including, for example, various solid and hematologically derived tumors, such as carcinomas, including, without limitation, cancer of the bladder, breast, colon, kidney, liver, lung (including small cell lung cancer), esophagus, gall-bladder, ovary, pancreas, stomach, endometrium, gastric, cervix, thyroid, prostate, uterus and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias (AML and CML), myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma), where such cancers have relapsed or become refractory. Cancers, such as prostate cancer, ovarian cancer, lung cancer, breast cancer, cholangiocarcinoma or other types of cancer, which have become refractory to anti-cancer treatment, such as with hormones, may also be treated with AMG 900 in the dosage regimen of the present invention.

The invention also provides a method for the treatment of solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

Besides being useful for human treatment, the compound is also useful for veterinary treatment of companion animals, exotic animals and farm animals, including mammals, rodents, and the like. For example, animals including horses, dogs, and cats may be similarly treated with AMG 900 for cancers.

Formulations

AMG 900 may be administered to the cancer subject as a single pharmaceutical compositions or medicament, comprising the active pharmaceutical ingredient AMG 900 (API), i.e., (N-(4-((3-(2-amino-4-pyrimidinyl)-2-pyridinyl)oxy)phenyl)-4-(4-methyl-2-thienyl)-1-phthalazinamine), in association with one or more non-toxic, pharmaceutically-acceptable carriers, diluents and/or adjuvants (collectively referred to herein as "excipient" materials). AMG 900, or a pharmaceutically acceptable salt form thereof, can be processed in accordance with conventional methods of pharmacy to produce the medicinal and pharmaceutical compositions for administration to patients, including humans and other mammals.

The pharmaceutical composition may be administered to the subject by any suitable route, adapted to such a route, and in a dose effective for the refractory cancer treatment intended. The composition, or API, may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, and typically from about 1 to 500 mg. A suitable daily dose for a human or other mammal may vary widely depending on the condition of the patient and other factors, but, once again, can be determined using routine methods and practices.

The amount of the API (AMG 900) which is administered and the dosage regimen for treating the refractory cancer condition depends on a variety of factors, including the age, weight, sex and medical condition of the subject, the type of disease, the severity of the cancer, the route and frequency of administration, and the physical and chemical properties of AMG 900 or its particular form, including a specific salt form. Thus, a dosage regimen may vary. A daily dose of about 0.01 to 500 mg, advantageously between about 1 mg and about 100 mg, more advantageously about 10 mg and about 50 mg and even more advantageously between about 15 mg and about 40 mg may be appropriate.

In addition, the dose administered to the subject, such as a human, may be provided twice daily, in a formulation comprising half the daily dose recommended. Thus, in embodiment 86, the invention provides a method of treating cancer in a subject or human, the method comprising administering to the subject or human AMG 900 or a pharmaceutically acceptable salt thereof in a dosage regimen comprising a daily dose ranging from about 5 mg to about 100 mg.

In embodiment 87, the invention provides embodiments 57-78 or 86 herein the dose is administered twice daily to the subject or human.

In embodiment 88, the invention provides embodiments 57-78, 86 or 87 herein the dosage regimen comprises a dose ranging from about 10 mg to about 50 mg that is administered twice daily to the subject or human.

In embodiment 89, the invention provides embodiments 57-78 or 86-88 herein the dosage regimen comprises a dose ranging from about 5 mg to about 20 mg that is administered twice daily to the subject or human.

The dosage amount can be administered in one to four dosage units per day.

For therapeutic purposes, AMG 900 may be combined with one or more adjuvants or "excipients" appropriate to the indicated route of administration. If administered on a per dose basis, AMG 900 may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, AMG 900 and the excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the API(s).

In the case of psoriasis and other skin conditions, it may be preferable to apply a topical preparation of the AMG 900 to the affected area two to four times a day. Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of the active ingredient is 0.1 mg to 150 mg administered one to four, preferably one or two times daily. For topical administration, the API may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, AMG 900 may be employed with either paraffinic or a water-miscible ointment base. Alternatively, it may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

AMG 900 can also be administered by transdermal device. Preferably transdermal administration will be accomplished using a patch either of the reservoir and porous membrane type or of a solid matrix variety. In either case, AMG 900 is delivered continuously from the reservoir or microcapsules through a membrane into the active agent permeable adhesive, which is in contact with the skin or mucosa of the recipient. If AMG 900 is absorbed through the skin, a controlled and predetermined flow of AMG 900 is administered to the recipient. In the case of microcapsules, the encapsulating agent may also function as the membrane.

The oily phase of the emulsions may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the API in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for AMG 900. AMG 900 is preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. For example AMG 900 may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. AMG 900 may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectible preparation may also be a sterile injectible solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Combination Administration

The present invention further provides AMG 900 in combination with one or more additional pharmaceutically active compounds/agents. In a particular embodiment, the additional pharmaceutically active agent is an agent that can be used to treat a cancer, also referred to herein as a second anti-cancer agent. For example, the second anti-cancer agent can be selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof. It is noted that the additional pharmaceutically active anti-cancer compounds/agents may be a traditional small organic chemical molecules or can be macromolecules such as a proteins, antibodies, peptibodies, DNA, RNA or fragments of such macromolecules.

Examples of specific pharmaceutically active agents that can be used in the treatment of cancers and that can be used in combination with one or more compound of the present invention include: methotrexate; tamoxifen; fluorouracil; 5-fluorouracil; hydroxyurea; mercaptopurine; cisplatin; carboplatin; daunorubicin; doxorubicin; etoposide; vinblastine; vincristine; paclitaxel; thioguanine; idarubicin; dactinomycin; imatinib; gemcitabine; altretamine; asparaginase; bleomycin; capecitabine; carmustine; cladibrine; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab;

trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant and nelarabine, or a pharmaceutically acceptable salt thereof.

Additional pharmaceutically active agents that can be used in the treatment of cancers and that can be used in combination with AMG 900 include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

AMG 900 can also be used in combination with pharmaceutically active agents that treat nausea. Examples of agents that can be used to treat nausea include: dronabinol; granisetron; metoclopramide; ondansetron; and prochlorperazine; or a pharmaceutically acceptable salt thereof.

In addition, AMG 900 may be used in combination with C-met inhibitors, PI3-kinase inhibitors, B-raf inhibitors, other aurora kinase inhibitors, anti-mitotic agents including without limitation, taxanes, epothilones including without limitation, ixabepilone. For example AMG 900 can be used in combination with the anti-mitotic agents described in PCT published patent application WO2011031842, which specification, including the figures, is incorporated herein by reference in its entirety.

In addition, AMG 900 can be used in combination with other agents that can be used to treat cancer such as acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflornithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/ tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-N1; interferon alfa-n3; interferon alfacon-1; interferon alpha natural; interferon beta; interferon beta-1a; interferon beta-1b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+fluorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; pentosan polysulfate sodium; pentostatin; picibanil; pirarubicin; rabbit antithymocyte polyclonal antibody; polyethylene glycol interferon alfa-2a; porfimer sodium; raltitrexed; rasburicase; rhenium Re 186 etidronate; RII retinamide; romurtide; samarium (153 Sm) lexidronam; sargramostim; sizofiran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; tumor necrosis factor alpha natural; ubenimex; bladder cancer vaccine; Maruyama vaccine; melanoma lysate vaccine; valrubicin; verteporfin; virulizin; zinostatin stimalamer; abarelix; AE 941 (Aeterna); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; filgrastim SD01 (Amgen); galocitabine; gastrin 17 immunogen; HLA-B7 gene therapy (Vica1); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody (MAb) (Biomira); cancer MAb (Japan Pharmaceutical Development); HER-2 and Fc MAb (Medarex); idiotypic 105AD7 MAb (CRC Technology); idiotypic CEA MAb (Trilex); LYM-1-iodine 131 MAb (Techniclone); polymorphic epithelial mucin-yttrium 90 MAb (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (SUGEN); TA 077 (Tanabe); tetrathiomolybdate; thaliblastine; thrombopoietin; tin ethyl etiopurpurin; tirapazamine; cancer vaccine (Biomira); melanoma vaccine (New York University); melanoma vaccine (Sloan Kettering Institute); melanoma oncolysate vaccine (New York Medical College); viral melanoma cell lysates vaccine (Royal Newcastle Hospital); or valspodar. It is noted that the agents recited above may also be administered as pharmaceutically acceptable salts when appropriate.

The compounds of the present invention may also be used in combination with radiation therapy, hormone therapy, surgery and immunotherapy, which therapies are well know to those skilled in the art.

The compounds of the present invention can be used in the manufacture of a medicament for the treatment of the diseases or conditions recited herein.

Thus, the combination of AMG 900 and the second anti-cancer agent independently can be formulated as separate compositions that are administered simultaneously or sequentially at different times, or both API's can be formulated as a single formulation, such as a tablet, capsule or injectable solution, and co-administration in a substantially simultaneous manner as a single composition. The invention includes an orally administrable form, such as a single capsule, having a fixed ratio of both active pharmaceutical ingredients (API) or multiple, separate unit dosage forms for each agent (API).

The phrase "co-administration", "co-therapy" or "combination-therapy", in defining the use of AMG 900 in the present invention is intended to embrace administration of the drug combination in a sequential manner in a regimen that will provide beneficial effects.

The foregoing is merely illustrative of the invention and is not intended to limit the invention to the disclosed uses. Variations and changes, which are routine to one skilled in the art, are intended to be within the scope and nature of the invention, which are defined in the appended claims. All mentioned references, patents, applications and publications, are hereby incorporated by reference in their entirety, as if here written.

What is claimed is:

1. A method of treating cancer in a human comprising administering to the human a dosage regimen comprising administering AMG 900, or a pharmaceutically acceptable salt thereof, orally to the human for 4, 5, 6 or 7 consecutive days, a once daily dose ranging from about 1 mg to about 80 mg.

2. The method of claim 1 wherein AMG 900, or a pharmaceutically acceptable salt thereof, is administered in a once daily dose ranging from about 5 mg to about 45 mg.

3. The method of claim 1 wherein AMG 900, or a pharmaceutically acceptable salt thereof, is administered in a once daily dose ranging from about 16 mg to about 35 mg.

4. The method of claim 1 wherein AMG 900, or a pharmaceutically acceptable salt thereof, is administered in a once daily dose ranging from about 20 mg to about 25 mg.

5. The method of claim 1 wherein AMG 900, or a pharmaceutically acceptable salt thereof, is administered in a once daily dose of about 24 mg.

6. The method of claim 1 wherein AMG 900 is administered in a once daily dose ranging from about 40 mg to about 80 mg.

7. The method of claim 1 wherein the dosage regimen comprises orally administering AMG 900, or a pharmaceutically acceptable salt thereof, to the human for 4 consecutive days.

8. The method of claim 1 wherein the dosage regimen comprises orally administering AMG 900, or a pharmaceutically acceptable salt thereof, to the human for 7 consecutive days.

9. The method of claim 1 wherein the dosage regimen comprises orally administering AMG 900, or a pharmaceutically acceptable salt thereof, to the human for 4, 5, 6 or 7 consecutive days followed immediately by non-treatment of AMG 900, or a pharmaceutically acceptable salt thereof, for a period ranging from 6 to 20 consecutive days.

10. The method of claim 1 wherein the dosage regimen comprises orally administering AMG 900, or a pharmaceutically acceptable salt thereof, to the human for 4 or 7 consecutive days followed immediately by non-treatment of AMG 900, or a pharmaceutically acceptable salt thereof, for a period ranging from 6 or 15 consecutive days.

11. The method of claim 1 wherein the dosage regimen further comprises administering AMG 900, or a pharmaceutically acceptable salt thereof, in combination with GCSF.

12. The method of claim 11 wherein the GCSF is administered in an amount ranging from about 5 mcg/kg to about 200 mcg/kg by weight of the human.

13. The method of claim 11 wherein AMG 900, or a pharmaceutically acceptable salt thereof, is administered in a once daily dose ranging from about 20 mg to about 40 mg in combination with GCSF administered in an amount ranging from about 5 mcg/kg to about 200 mcg/kg by weight of the human.

14. The method of claim 1 wherein the dosage regimen further comprises fasting the human for at least one hour immediately prior to administering AMG 900, or a pharmaceutically acceptable salt thereof, and for at least another 2 hours immediately after administering AMG 900, or a pharmaceutically acceptable salt thereof.

15. The method of claim 1 wherein the cancer is one or more of (a) a solid or hematologically derived tumor selected from (a) cancer of the bladder, breast, colon, kidney, liver, lung, small cell lung cancer, esophagus, gall-bladder, ovary, endometrium, pancreas, stomach, uterus, cervix, thyroid, brain, prostate and skin, (b) a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma, (c) a hematopoietic tumor of myeloid lineage selected from acute and chronic myelogenous leukemias, myelodysplastic syndrome and promyelocytic leukemia (d) a tumor of mesenchymal origin selected from fibrosarcoma and rhabdomyosarcoma, (e) a tumor of the central and peripheral nervous system selected from astrocytoma, neuroblastoma, glioma and schwannoma, and (f) a melanoma, seminoma, teratocarcinoma, osteosarcoma, xenoderoma pigmentosum, keratoctanthoma, thyroid follicular cancer or Kaposi's sarcoma.

16. The method of claim 1 wherein the cancer is one or more of a solid tumor selected from cancer of the bladder, breast, colon, kidney, liver, lung, non-small cell lung, head and neck, esophageal, gastric, ovary, endometrium, pancreas, stomach, uterus, cervix, thyroid, brain and prostate or a lymphoma or leukemia, or a combination thereof.

17. The method of claim 1 wherein the cancer is a solid cancer tumor of the prostate, ovary, endometrium, breast, bladder, colon, kidney, liver, lung, esophagus, pancreas, stomach, uterus, cervix, thyroid, brain or skin, or a combination thereof.

18. The method of claim 1 wherein the cancer is (a) a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma or (b) a hematopoietic tumor of myeloid lineage selected from acute and chronic myelogenous leukemias, myelodysplastic syndrome and promyelocytic leukemia, or a combination thereof.

19. The method of claim 1 wherein the cancer is a hematopoietic tumor of myeloid lineage selected from acute and chronic myelogenous leukemias, myelodysplastic syndrome and promyelocytic leukemia, or a combination thereof.

20. The method of claim 1 wherein the cancer is selected from the group consisting of prostate cancer, neuroendocrine cancer, ovarian cancer, endometrial cancer, breast cancer, uterine cancer and cervical cancer, or a combination thereof.

21. The method of claim 1 wherein the dosage regimen comprises administering AMG 900, or a pharmaceutically acceptable salt thereof, in combination with a second anti-cancer agent.

22. The method of claim 21 wherein the second anti-cancer agent is methotrexate; tamoxifen; fluorouracil; 5-fluorouracil; hydroxyurea; mercaptopurine; cisplatin; carboplatin; daunorubicin; doxorubicin; etoposide; vinblastine; vincristine; paclitaxel; thioguanine; idarubicin; dactinomycin; imatinib; gemcitabine; altretamine; asparaginase; bleomycin; capecitabine; carmustine; cladibrine; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant or nelarabine, or a combination thereof.

23. The method of claim 1 wherein the dosage regimen comprises fasting the human for one hour immediately prior to and for two hours immediately after administering the once daily dose of AMG 900, or a pharmaceutically acceptable salt thereof.

24. The method of claim 9 wherein the cancer is selected from the group consisting of prostate cancer, neuroendocrine cancer, ovarian cancer, endometrial cancer, breast cancer, uterine cancer and cervical cancer, or a combination thereof.

25. The method of claim 24 wherein the cancer is ovarian cancer.

26. The method of claim 24 wherein the cancer is breast cancer.

27. The method of claim 24 wherein the cancer is prostate cancer.

28. The method of claim 9 wherein the dosage regimen comprises orally administering AMG 900, or a pharmaceutically acceptable salt thereof, to the human once daily for 4 consecutive days followed immediately by non-treatment of the AMG 900 for a period of 10 consecutive days.

29. The method of claim 28 wherein the once daily dose of AMG 900 or a pharmaceutically acceptable salt thereof, is an amount ranging from about 16 mg to about 40 mg.

30. The method of claim 9 wherein the dosage regimen comprises orally administering AMG 900, or a pharmaceutically acceptable salt thereof, to the human once daily for 7 consecutive days followed immediately by non-treatment of the AMG 900 for a period of 7 consecutive days.

31. The method of claim 30 wherein the once daily dose of AMG 900 or a pharmaceutically acceptable salt thereof, is an amount ranging from about 10 mg to about 80 mg.

* * * * *